United States Patent
Ahlquist et al.

(10) Patent No.: US 7,611,833 B2
(45) Date of Patent: Nov. 3, 2009

(54) YEAST GENES THAT AFFECT VIRAL REPLICATION

(75) Inventors: Paul G. Ahlquist, Madison, WI (US); Masayuki Ishikawa, Sapporo (JP); Juana Diez, Barcelona (ES); Duane B. Price, Mountain Brook, AL (US); Wai-Ming Lee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 702 days.

(21) Appl. No.: 10/618,896

(22) Filed: Jul. 14, 2003

(65) Prior Publication Data

US 2006/0247196 A1 Nov. 2, 2006

Related U.S. Application Data

(63) Continuation of application No. 09/760,040, filed on Jan. 12, 2001, now abandoned.

(51) Int. Cl.
*C12Q 1/00* (2006.01)
*G01N 33/53* (2006.01)
*A01N 61/00* (2006.01)
*C07K 1/00* (2006.01)

(52) U.S. Cl. .......................... 435/4; 435/7.71; 530/350; 514/1

(58) Field of Classification Search ..................... 435/4, 435/7.71; 530/350; 514/1
See application file for complete search history.

(56) References Cited

OTHER PUBLICATIONS

Rudinger, 1976, Peptide Hormones, Parsons, University Park Press, Baltimore, p. 1-7.*
Kaye et al., 1990, Proc. Natl. Acad. Sci. USA, vol. 87, pp. 6922-6926.*
Skolnick et al., 2000, Trends in Biotech, vol. 18, p. 34-39.*
P. Ahlquist, et al., "Bromovirus and Nodavirus RNA Replication," Sixth International Symposium on Positive Strand RNA Viruses, S3-06, May 28-Jun. 2, 2001, Institut Pasteur, Paris, France (abstract).
T. Baumstark and P. Ahlquist, "The Brome Mosaic Virus RNA3 Intergenic Replication Enhancer Folds to Mimic a tRNA TYC-stem Loop and is Modified In Vivo," Sixth international Symposium on Positive Strand RNA Viruses, P1-127, May 28-Jun. 2, 2001, Institut Pasteur, Pari, France.
T. Baumstark and P. Ahlquist, "The Brome Mosaic Virus RNA3 Intergenic Replication Enhancer Folds to Mimic a tRNA TYC-stem Loop and is Modified In Vivo," American Society for Virology, W16-4, 20th Annual Meeting, Unversity of Wisconsin-Madison, Madison, Wisconsin, Jul. 21-25.
A.J. Caplan, at al., "Characterization of YDJ1: A Yeast Homologue of the Bacterial dnaJ Protein," J. Cell Biol. 114(4):609-621, 1991 (front page only).
A.J. Caplan, et al., "YDJ1p Facilitates Polypeptide Translocation across Different Intracellular Membranes by a Conserved Mechanism," Cell 71:1143-1155, 1992 (front page only).

J. Chen, et al., "Brome Mosaic Virus Replication Protein 1a Recruits Viral RNA2 to Replication through a 5'-Proximal RNA2 Replication Signal," American Society for Virology, 19th Annual Meeting, Colorado State University, Fort Collins, Colorado, p. 129, Jul. 8-12, 2000 (abstract).
J. A. den Boon, et al., "Identification of Sequences in Brome Mosaic Virus Replicase Protein 1A that Mediate Association with Endoplasmic Reticulum Membranes," Sixth International Symposium on Positive Strand RNA Viruses, P1-128, May 28-Jun. 2, 2001, Institut Pasteur.
J.A. den Boon, et al., "Sequences in the N-Terminal Capping Domain of Brome Mosaic Virus Replicase Protein 1A Mediate Association with Endoplasmic Reticulum Membranes," American Society for Virology, W30-8, 20th Annual Meeting, University of Wisconsin-Madison, Madison.
J. Diez, et al., "Identification and Characterization of a Host Protein Factor Involved in Template Selection for Viral RNA Replication," American Society for Virology, 19th Annual Meeting, Colorado State University, Fort Collins, Colorado, p. 128, Jul. 8-12, 2000 (abstract).
J. Diez, et al., "Identification and Characterization of a Host Protein Factor Involved in Template Selection for Viral RNA Replication," PNAS 97(8):3913-3918, 2000.
H. Hermann, et al., "snRNP Sm Proteins Share Two Evolutionarily Conserved Sequence Motifs which are Involved in Sm Protein-Protein Interactions," EMBO J. 14(9):2076-2088, 1995 (front page only).
J. Hu, et al., Hepadnavirus Assembly and Reverse Transcription Require a Multi-Component Chaperone Complex which is Incorporated into Nucleocapsids, EMBO J. 16(1):59-68, 1997.
M. Ishikawa, et al., "In Vivo DNA Expression of Functional Brome Mosaic Virus RNA Replicons in *Saccharomyces cerevislae*," J. Virol. 71(10):7781-7790, 1997.
M. Ishikawa, et al., "Yeast Mutations in Multiple Complementation Groups Inhibit Brome Mosaic Virus RNA Replication and Transcription and Perturb Regulated Expression of the Viral Polymerase-Like Gene," Proc. Natl. Acad. Sci. USA 94:7781-7790, 1997.
M. Janda and P. Ahlquist, "RNA-Dependent Replication, Transcription, and Persistence of Brome Mosaic Virus RNA Replicons in *S. cerevislae*," Cell 72:961-970, 1993.
M. Janda and P. Ahlquist, "Brome Mosaic Virus RNA Replication Protein 1a Dramatically Increases In Vivo Stability but not Translation of Viral Genomic RNA3," Proc. Natl. Acad. Sci. USA 95:2227-2232, 1998.
Y. Kimura, et al., "Role of the Protein Chaperone YDJ1 in Establishing Hsp9O-Mediated Signal Transduction Pathways," Science 268:1362 (front page only), 1995.
D.B. Kushner and P. Ahlquist, "Turnover, Host-mediated Repair and Replication of 3' tRNA-like Ends of Brome Mosaic Virus RNA In Vivo," Sixth International Symposium on Positive Strand RNA Viruses, P1-127, May 28-Jun. 2, 2001, Institut Pasteur, Paris, France (abstract).

(Continued)

*Primary Examiner*—Shin-Lin Chen
(74) *Attorney, Agent, or Firm*—Quarles & Brady LLP

(57) ABSTRACT

An antiviral agent comprising an altered MAB1, MAB2, MAB3, or OLE1 gene, gene homologs or related genes is disclosed. In another embodiment, the present invention is a method of creating a virus resistant organism comprising creating a transgenic organism comprising an antiviral agent selected from the group of altered MAB1 genes, MAB2 genes, MAB3 genes or OLE1 genes, homologs of these genes, related genes and combinations of these genes and homologs.

4 Claims, 12 Drawing Sheets

OTHER PUBLICATIONS

Figure 1:
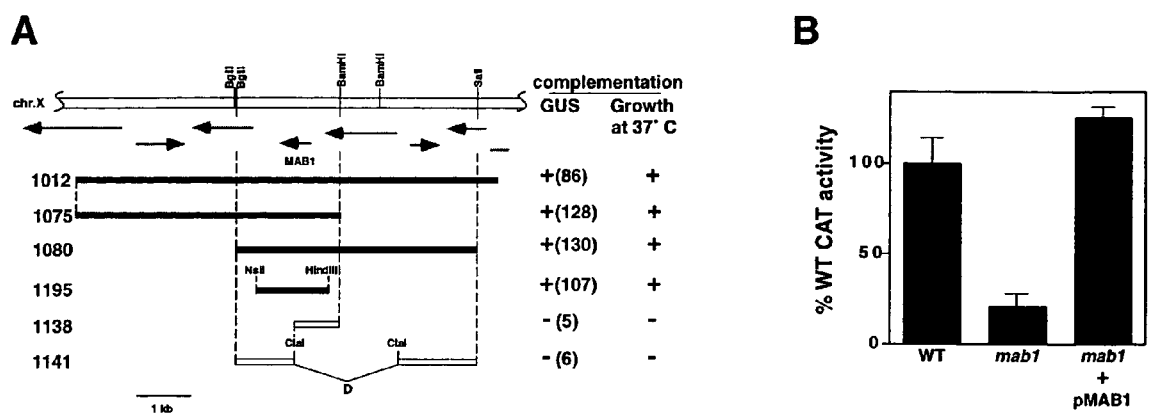

D.B. Kushner and P. Ahlquist, "Turnover, Host-mediated Repair and Replication of 3 tRNA-like Ends of Brome Mosaic Virus RNA In Vivo," American Society for Virology, W16-10, 20th Annual Meeting, University of Wisconsin-Madison, Madison, Wisconsin, Jul. 21-25, 2001 (abstract).

D.H. Lee, et al., "Involvement of the Molecular Chaperone Ydj1 in the Ubiquitin-Dependent Degradation of Short-Lived and Abnormal Proteins in *Saccharomyces cerevisiae*," Mole. Cell. Biol. 16(9):4773-4781, 1996 (front page only).

W.-M. Lee, et al., "Altered Membrane Lipid Composition Inhibits Formation of Functional Brome Mosaic Virus RNA Replication Complexes," American Society for Virology, 19th Annual Meeting, Colorado State University, Fort Collins, Colorado, p. 129, Jul. 8-12, 2000 (abstract).

W.-M. Lee, et al., "Mutation of Host delta9 Fatty Acid Desaturase Inhibits Brome Mosaic Virus RNA Replication between Template Recognition and RNA Synthesis," J. Virol. 75(5):2097-2106, 2001.

B.D. Lindenbach, et al., "A Long Distance Interaction in Flock House Virus RNA1 Controls Subgenomic RNA3 Synthesis," Sixth International Symposium on Positive Strand RNA Viruses, P1-129, May 28-Jun. 2, 2001, Institut Pasteur, Paris, France (abstract).

B.D. Lindenbach, et al., "Flock House Virus Subgenomic RNA3 Synthesis is Controlled by a Long Distance Base Pairing Interaction in RNA1," American Society for Virology, W3-2, 20th Annual Meeting, University of Wisconsin-Madison, Madison, Wisconsin, Jul. 21-25, 2001 (abstract).

A.E. McBride, et al., "Human Protein Sam68 Relocalization and Interaction with Poliovirus RNA Polymerase in Infected Cells," Proc. Natl. Acad. Sci. USA 93:2296-2301, 1996.

D.J. Miller, et al., "Flock House Virus RNA Replicates on the Outer Mitochondrial Membrane of Drosophila Cells," American Society for Virology, W41-4, 20th Annual Meeting, University of Wisconsin-Madison, Madison, Wisconsin, Jul. 21-25, 2001 (abstract).

E.J. Neer, at al., "The Ancient Regulatory-Protein Family of WD-Repeat Proteins," Nature 371:297-300, 1994.

A. Noueiry and P. Ahlquist, "A Mutant Allele of DED1, A Yeast General Translation Initiation Factor, Selectively Inhibits Translation of Bromovirus Polymerase Message," American Society for Virology, 19th Annual Meeting, Colorado State University, Fort Collins, Colorado, p. 88, Jul. 8-12, 2000 (abstract).

A. Noueiry, et al., "A Mutant Allele of Essential, General Translation Initiation Factor DED1 Selectively Inhibits Translation of a Viral mRNA," PNAS 97(24):12985-12990, 2000.

A. Noueiry, et al., "BMV RNA Translation Requires Host Genes Essential for Deadenylated mRNA Decapping," Sixth International Symposium on Positive Strand RNA Viruses, S3-O6, May 28-Jun. 2, 2001, Institut Pasteur, Parison, France (abstract).

A. Neueiry, et al., "BMV RNA Translation Require Host Genes Essential for Deadenylated mRNA Decapping," American Society for Virology, W17-3, 20th Annual Meeting, University of Wisconsin-Madison, Madison, Wisconsin, Jul. 21-25, 2001 (abstract).

R.E. O'Neill, at al., "Nuclear Import of Influenza Virus RNA can be Mediated by Viral Nucleoprotein and Transport Factors Required for Protein Import," J. Biol. Chem. 270(39):22701-22704, 1995.

R.E. O'Neill, et al., "NPI-1, the Human Homolog of SRP-1, Interacts with Influenza Virus Nucleoprotein," Virology 206:116-125, 1995.

B.D. Price, et al., "Induction of RNA Replicons Based on Flock House Virus RNA2 that Express Replication-dependent Selectable Markers in *S. cerevisiae*," American Society for Virology, 19th Annual Meeting, Colorado State University, Fort Collins, Colorado, p. 129, Jul. 8-12, 2000.

M.A. Restrepo-Hartwig and P. Ahlquist, "Brome Mosaic Virus Helicase- and Polymerase-Like Proteins Colcalize on the Endoplasmic Reticulum at Sites of Viral RNA Synthesis," J. Virol. 70(12):a-j, 1996.

V.E. Velculescu, at al., "Characterization of the Yeast Transcriptome," Cell 88:243-251, 1997 (front page only).

Li et al (1994) Int J Cancer 57:348-352.

Dias and Parsons (1995) J Lipid Res 36:552-563.

GenBank accession No. Y13647; Jun. 6, 1997.

Zhang et al. (1999) Biochem J 340:255-264.

St John et al (1991) J Animal Sci 69:1064-1073.

Ward et al (1997) Biochem Soc Trans 25:s673.

GenBank accession No. AU055693; Mar 29, 1999.

Chung et al. (2000) Biosci Biotech Biochem 64:1526-1530.

Ahlquist P (2006) Parallels among positive-strand RNA viruses, reverse-transcribing viruses and double-stranded RNA viruses. Nat Rev Microbiol 4: 371-382.

Lee, W-M., M. Ishikawa and P. Ahlquist (2001). Mutation of host Δ9 fatty acid desaturase inhibits brome mosaic virus RNA replication between template recognition and RNA synthesis. J. Virol. 75:2097-2106.

Lee, W-M. and P. Ahlquist (2003). Membrane synthesis, specific lipid requirements, and localized lipid composition changes associated with a positive-strand RNA virus RNA replication protein. J. Virol. 77: 12819-12828.

Mackenzie J (2005) Wrapping things up about virus RNA replication. Traffic 6: 967-977.

Miller, D. J., M. D. Schwartz, B. T. Dye and P. Ahlquist (2003). Engineered retargeting of viral RNA replication complexes to an alternative intracellular membrane. J. Virol. 77:12193-12202.

Miyanari Y, Hijikata M, Yamaji M, Hosaka M, Takahashi H, Shimotohno K (2003) Hepatitis C virus non-structural proteins in the probable membranous compartment function in viral genome replication. J Biol Chem 278:50301-8.

Quinkert D, Bartenschlager R, Lohmann V (2005) Quantitative analysis of the hepatitis C virus replication complex. J Virol. 79:13594-605.

Salonen A, Ahola T, Kääriäinen L (2005) Viral RNA replication in association with cellular membranes. Curr Top Microbiol Immunol. 285:139-73.

Schwartz, M., J. Chen, M. Janda, M. Sullivan, J. den Boon and P. Ahlquist (2002). A positive-strand RNA virus replication complex parallels form and function of retrovirus capsids. Molecular Cell 9:505-514.

Schwartz, M., J. Chen, W-M Lee, M. Janda and P. Ahlquist (2004). Alternate, virus-induced membrane rearrangements support positive-strand RNA virus genome replication. Proc. Natl. Acad. Sci. USA 101:11263-11268.

http://www.genecards.org/cgi-bin/carddisp.pl?gene=SCD&search=scd1&suff=txt.

* cited by examiner

```
                         SEQUENCE LISTING

<160> NUMBER OF SEQ ID NOS: 22

<210> SEQ ID NO 1
<211> LENGTH: 32
<212> TYPE: PRT
<213> ORGANISM: Saccharomyces cerevisiae

<400> SEQUENCE: 1

Leu Arg Val Leu Thr Gln Asp Gly Arg Val Tyr Ile Gly Gln Leu Met
1               5                   10                  15

Ala Phe Asp Lys His Met Asn Leu Val Leu Asn Glu Cys Ile Glu Glu
            20                  25                  30

<210> SEQ ID NO 2
<211> LENGTH: 14
<212> TYPE: PRT
<213> ORGANISM: Saccharomyces cerevisiae

<400> SEQUENCE: 2

Leu Gly Leu Thr Ile Leu Arg Gly Glu Gln Ile Leu Ser Thr
1               5                   10

<210> SEQ ID NO 3
<211> LENGTH: 32
<212> TYPE: PRT
<213> ORGANISM: Saccharomyces cerevisiae

<400> SEQUENCE: 3

Val Thr Ile Glu Leu Lys Asn Gly Thr Thr Val Trp Gly Thr Leu Gln
1               5                   10                  15

Ser Val Ser Pro Gln Met Asn Ala Ile Leu Thr Asp Val Lys Leu Thr
            20                  25                  30
```

-continued

```
<210> SEQ ID NO 4
<211> LENGTH: 14
<212> TYPE: PRT
<213> ORGANISM: Saccharomyces cerevisiae

<400> SEQUENCE: 4

Leu Gln Tyr Ile Asn Ile Arg Gly Asn Thr Ile Arg Gln Ile
1               5                   10

<210> SEQ ID NO 5
<211> LENGTH: 32
<212> TYPE: PRT
<213> ORGANISM: Saccharomyces cerevisiae

<400> SEQUENCE: 5

Ile Trp Leu Phe Glu Gln Ile Gly Ile Arg Ile Lys Gly Lys Ile Val
1               5                   10                  15

Gly Phe Asp Glu Phe Met Asn Val Val Ile Asp Glu Ala Val Glu Ile
            20                  25                  30

<210> SEQ ID NO 6
<211> LENGTH: 14
<212> TYPE: PRT
<213> ORGANISM: Saccharomyces cerevisiae

<400> SEQUENCE: 6

Leu Gly Lys Ile Leu Leu Lys Gly Asp Asn Ile Thr Leu Ile
1               5                   10

<210> SEQ ID NO 7
<211> LENGTH: 33
<212> TYPE: PRT
<213> ORGANISM: Saccharomyces cerevisiae

<400> SEQUENCE: 7

Val Gly Val Lys Leu Lys Phe Asn Ser Thr Glu Tyr Arg Gly Thr Leu
1               5                   10                  15

Val Ser Thr Asp Asn Tyr Phe Asn Leu Gln Leu Asn Glu Ala Glu Glu
            20                  25                  30

Phe

<210> SEQ ID NO 8
<211> LENGTH: 14
<212> TYPE: PRT
<213> ORGANISM: Saccharomyces cerevisiae

<400> SEQUENCE: 8

Leu Gly Glu Ile Phe Ile Arg Cys Asn Asn Val Leu Tyr Ile
1               5                   10

<210> SEQ ID NO 9
<211> LENGTH: 32
<212> TYPE: PRT
<213> ORGANISM: Saccharomyces cerevisiae

<400> SEQUENCE: 9

Ile Leu Leu Asn Ile Asn Gly Ser Arg Lys Val Ala Gly Ile Leu Arg
1               5                   10                  15

Gly Tyr Asp Ile Phe Leu Asn Val Val Leu Asp Asp Ala Met Glu Ile
            20                  25                  30
```

<210> SEQ ID NO 10
<211> LENGTH: 14
<212> TYPE: PRT
<213> ORGANISM: Saccharomyces cerevisiae

<400> SEQUENCE: 10

Ile Gly Met Val Val Ile Arg Gly Asn Ser Ile Ile Met Leu
1               5                   10

<210> SEQ ID NO 11
<211> LENGTH: 32
<212> TYPE: PRT
<213> ORGANISM: Saccharomyces cerevisiae

<400> SEQUENCE: 11

Ile Phe Val Leu Leu Arg Asp Gly Arg Met Leu Phe Gly Val Leu Arg
1               5                   10                  15

Thr Phe Asp Gln Tyr Ala Asn Leu Ile Leu Gln Asp Cys Val Glu Arg
            20                  25                  30

<210> SEQ ID NO 12
<211> LENGTH: 14
<212> TYPE: PRT
<213> ORGANISM: Saccharomyces cerevisiae

<400> SEQUENCE: 12

Arg Gly Ile Phe Met Ile Arg Gly Glu Asn Val Val Met Leu
1               5                   10

<210> SEQ ID NO 13
<211> LENGTH: 31
<212> TYPE: PRT
<213> ORGANISM: Schizosaccharomyces pombe

<400> SEQUENCE: 13

Ile Val Val Leu Arg Asp Gly Lys Lys Leu Ile Gly Ile Leu Arg Ser
1               5                   10                  15

Phe Asp Gln Phe Ala Asn Leu Met Leu Gln Tyr Thr Ile Glu Arg
            20                  25                  30

<210> SEQ ID NO 14
<211> LENGTH: 14
<212> TYPE: PRT
<213> ORGANISM: Schizosaccharomyces pombe

<400> SEQUENCE: 14

Arg Gly Val Tyr Ile Val Arg Gly Glu Asn Val Val Leu Leu
1               5                   10

<210> SEQ ID NO 15
<211> LENGTH: 31
<212> TYPE: PRT
<213> ORGANISM: Homo sapiens

<400> SEQUENCE: 15

Leu Val Leu Leu Arg Asp Gly Arg Thr Leu Ile Gly Phe Leu Arg Ser
1               5                   10                  15

Ile Asp Gln Phe Ala Asn Leu Val Leu His Gln Thr Val Glu Arg
            20                  25                  30

<210> SEQ ID NO 16
<211> LENGTH: 14
<212> TYPE: PRT
<213> ORGANISM: Homo sapiens

```
<400> SEQUENCE: 16

Arg Gly Ile Phe Val Val Arg Gly Glu Asn Val Val Leu Leu
 1               5                  10

<210> SEQ ID NO 17
<211> LENGTH: 31
<212> TYPE: PRT
<213> ORGANISM: Caenorhabditis elegans

<400> SEQUENCE: 17

Leu Val Val Leu Arg Asp Gly Arg Lys Leu Ile Gly Phe Leu Arg Ser
 1               5                  10                  15

Ile Asp Gln Phe Ala Asn Leu Ile Leu Glu Asp Val Val Glu Arg
            20                  25                  30

<210> SEQ ID NO 18
<211> LENGTH: 14
<212> TYPE: PRT
<213> ORGANISM: Caenorhabditis elegans

<400> SEQUENCE: 18

Gln Gly Phe Met Leu Ile Arg Gly Glu Asn Val Glu Leu Ala
 1               5                  10

<210> SEQ ID NO 19
<211> LENGTH: 32
<212> TYPE: PRT
<213> ORGANISM: Saccharomyces cerevisiae

<400> SEQUENCE: 19

Leu Ile Val Ser Thr Leu Glu Asp Arg Ile Leu Val Gly Ser Leu Val
 1               5                  10                  15

Ala Val Asp Ala Gln Met Asn Leu Leu Leu Asp His Val Glu Glu Arg
            20                  25                  30

<210> SEQ ID NO 20
<211> LENGTH: 14
<212> TYPE: PRT
<213> ORGANISM: Saccharomyces cerevisiae

<400> SEQUENCE: 20

Gly Leu Val Ser Val Pro Arg Arg Ser Val Lys Thr Ile Met
 1               5                  10

<210> SEQ ID NO 21
<211> LENGTH: 33
<212> TYPE: PRT
<213> ORGANISM: Artificial
<220> FEATURE:
<223> OTHER INFORMATION: conserved sequence of Sm motif 1
<220> FEATURE:
<221> NAME/KEY: MISC_FEATURE
<222> LOCATION: (1)..(1)
<223> OTHER INFORMATION: X is a hydrophobic amino acid
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X is a hydrophobic amino acid
<220> FEATURE:
<221> NAME/KEY: MISC_FEATURE
<222> LOCATION: (4)..(4)
<223> OTHER INFORMATION: X can be any amino acid
```

```
<220> FEATURE:
<221> NAME/KEY: MISC_FEATURE
<222> LOCATION: (6)..(11)
<223> OTHER INFORMATION: X can be any amino acid
<220> FEATURE:
<221> NAME/KEY: MISC_FEATURE
<222> LOCATION: (12)..(12)
<223> OTHER INFORMATION: X is a hydrophobic amino acid
<220> FEATURE:
<221> NAME/KEY: MISC_FEATURE
<222> LOCATION: (13)..(13)
<223> OTHER INFORMATION: X can be any amino acid
<220> FEATURE:
<221> NAME/KEY: MISC_FEATURE
<222> LOCATION: (15)..(15)
<223> OTHER INFORMATION: X can be any amino acid
<220> FEATURE:
<221> NAME/KEY: MISC_FEATURE
<222> LOCATION: (16)..(16)
<223> OTHER INFORMATION: X is a hydrophobic amino acid
<220> FEATURE:
<221> NAME/KEY: MISC_FEATURE
<222> LOCATION: (17)..(19)
<223> OTHER INFORMATION: X can be any amino acid
<220> FEATURE:
<221> NAME/KEY: MISC_FEATURE
<222> LOCATION: (21)..(22)
<223> OTHER INFORMATION: X can be any amino acid
<220> FEATURE:
<221> NAME/KEY: MISC_FEATURE
<222> LOCATION: (25)..(25)
<223> OTHER INFORMATION: X is a hydrophobic amino acid
<220> FEATURE:
<221> NAME/KEY: MISC_FEATURE
<222> LOCATION: (26)..(26)
<223> OTHER INFORMATION: X can be any amino acid
<220> FEATURE:
<221> NAME/KEY: MISC_FEATURE
<222> LOCATION: (27)..(27)
<223> OTHER INFORMATION: X is a hydrophobic amino acid
<220> FEATURE:
<221> NAME/KEY: MISC_FEATURE
<222> LOCATION: (28)..(31)
<223> OTHER INFORMATION: X can be any amino acid
<220> FEATURE:
<221> NAME/KEY: MISC_FEATURE
<222> LOCATION: (33)..(33)
<223> OTHER INFORMATION: X can be any amino acid

<400> SEQUENCE: 21

Xaa Xaa Xaa Xaa Leu Xaa Xaa Xaa Xaa Xaa Xaa Xaa Xaa Gly Xaa Xaa
1               5                   10                  15

Xaa Xaa Xaa Asp Xaa Xaa Met Asn Xaa Xaa Xaa Xaa Xaa Xaa Xaa Glu
                20                  25                  30

Xaa

<210> SEQ ID NO 22
<211> LENGTH: 14
<212> TYPE: PRT
<213> ORGANISM: Artificial
<220> FEATURE:
<223> OTHER INFORMATION: conserved sequence of Sm motif 2
<220> FEATURE:
<221> NAME/KEY: MISC_FEATURE
<222> LOCATION: (1)..(1)
<223> OTHER INFORMATION: X is a hydrophobic amino acid
<220> FEATURE:
<221> NAME/KEY: MISC_FEATURE
<222> LOCATION: (1)..(1)
<223> OTHER INFORMATION: X is a hydrophobic amino acid
<220> FEATURE:
<221> NAME/KEY: MISC_FEATURE
<222> LOCATION: (3)..(3)
<223> OTHER INFORMATION: X can be any amino acid
```

-continued

```
<220> FEATURE:
<221> NAME/KEY: MISC_FEATURE
<222> LOCATION: (4)..(6)
<223> OTHER INFORMATION: X is a hydrophobic amino acid
<220> FEATURE:
<221> NAME/KEY: MISC_FEATURE
<222> LOCATION: (9)..(9)
<223> OTHER INFORMATION: X can be any amino acid
<220> FEATURE:
<221> NAME/KEY: MISC_FEATURE
<222> LOCATION: (11)..(11)
<223> OTHER INFORMATION: X is a hydrophobic amino acid
<220> FEATURE:
<221> NAME/KEY: MISC_FEATURE
<222> LOCATION: (12)..(12)
<223> OTHER INFORMATION: X can be any amino acid
<220> FEATURE:
<221> NAME/KEY: MISC_FEATURE
<222> LOCATION: (13)..(14)
<223> OTHER INFORMATION: X is a hydrophobic amino acid

<400> SEQUENCE: 22

Xaa Gly Xaa Xaa Xaa Xaa Arg Gly Xaa Asn Xaa Xaa Xaa Xaa
1               5                   10
```

YEAST GENES THAT AFFECT VIRAL REPLICATION

CROSS-REFERENCE TO RELATED APPLICATION

This application is a continuation of Ser. No. 09/760,040, Jan. 12, 2001, now abandoned which claims the benefit of priority from U.S. Ser. No. 60/049,439, filed Jun. 12, 1997 and U.S. Ser. No. 09/094,069, filed Jun. 9, 1998. These applications are incorporated by reference herein.

STATEMENT REGARDING FEDERALLY SPONSORED RESEARCH OR DEVELOPMENT

This invention was made with United States Government support awarded by AID, Grant No. DHR-5542-G-SS-9034-00; NSF Grant No. DMB-8451884; MCB-9004385; IBN-9018503; and NIH, Grant No. GM35072; GM51301; AI23742. The United States Government has certain rights in this invention.

BACKGROUND OF THE INVENTION

Upon infection, the genomes of positive-strand RNA viruses are translated to yield a variety of proteins. Some of these direct the assembly of an RNA replication complex, which first synthesizes a negative-strand RNA replication intermediate and then uses this negative strand as a template for producing more positive-strand genomic RNAs. Several lines of evidence suggest that multiple steps in positive-strand RNA virus RNA replication depend on specific host factors. Different host cells show differing levels of permissiveness for various intracellular replication steps (W. De Jong and P. Ahlquist, *J. Virol.* 69:1485-1492, 1995; A. V. Gamarnik and R. Andino, *EMBO J.* 15:5988-5998, 1996). The replication complex of each virus assembles on specific membrane sites in the infected cell (S. Froshauer, et al., *J. Cell Biol.* 107:2075-2086, 1988; K. Bienz, et al., *J. Virol.* 66:2740-2747, 1992; M. Restrepo-Hartwig and P. Ahlquist, J. Virol. 70:8908-8916, 1996), and such association with cell membranes appears particularly important for positive-strand RNA synthesis (S. Wu, et al., *Proc. Natl. Acad. Sci. USA* 89:11136-11140, 1992). Partial purification of some positive-strand RNA replication complexes has shown them to involve complexes of viral and cellular proteins, and some of the cell proteins in such complexes have been implicated as potentially functional contributors to replication (R. Quadt, et al., *Proc. Natl. Acad. Sci. USA* 90:1498-1502, 1993; T. A. M. Osman and K. W. Buck, *J. Virol.* 71:6075-6082, 1997; Yamanaka, et al., *Proc. Natl. Acad. Sci. USA* 97:10107-10112, 2000).

To facilitate studying the mechanisms of positive-strand RNA virus replication and the nature and function of host proteins involved, we have shown that brome mosaic virus (BMV) RNAs and their derivatives can replicate and direct gene expression in the yeast *Saccharomyces cerevisiae*, the rapid growth, facile genetics, and completely sequenced genome of which offer potentially useful features for virus replication studies. BMV replication in yeast reproduces all known features of BMV RNA replication in naturally plant hosts, including localization of replication complexes to the endoplasmic reticulum, dependence on the same viral replication factors and on the same cis-acting RNA replication signals, similar ratios of positive to negative strand RNA, and other features (M. Janda and P. Ahlquist, *Cell* 72:961-970, 1993; M. Sullivan and P. Ahlquist, *J. Virol.* 73:2622-2632; M. Ishikawa, et al., *J. Virol.* 71:7781-7790, 1997; M. Restrepo-Hartwig and P. Ahlquist, *J. Virol.* 73:10303-10309, 1999; R. Quadt, et al., *Proc. Natl. Acad. Sci. USA* 92:4892-4896, 1995).

BMV encodes two RNA replication factors, 1a and 2a, containing three domains conserved throughout the large alphavirus-like superfamily of animal and plant viruses (P. Ahlquist, *Curr. Opin. Genet. Dev.* 2:71-76, 1992). BMV1a (109 kDa) contains an N-proximal helicase-like domain, whereas 2a (94 kDa) contains a central polymerase-like domain. BMV1a and 2a interact (C. C. Kao, et al., *J. Virol.* 66:6322-6329, 1992; C. C. Kao and P. Ahlquist, *J. Virol.* 66:7293-7302, 1992; E. Smirnyagina, et al., *J. Virol.* 70:4729-4736, 1996) and in vivo colocalize on the endoplasmic reticulum at the sites of BMV RNA synthesis (M. Restrepo-Hartwig and P. Ahlquist, supra, 1996). BMV 1a and 2a are encoded by BMV RNA1 and RNA2, respectively. A third genomic RNA, RNA3, encodes the 3a cell-to-cell movement protein and the coat protein, which are required for BMV infection spread in its natural plant hosts but are dispensable for RNA replication (R. Allison, et al., *Proc. Natl. Acad. Sci. USA* 87:1820-1824, 1990; K. Mise and P. Ahlquist, *Virology* 206:276-286, 1995). The 3'-proximal coat gene is not translatable from RNA3 but only from a subgenomic mRNA, RNA4, synthesized from negative-strand RNA3 (FIG. 1). Host factor involvement in BMV RNA replication is suggested by host-specific replication effects, biochemical studies, and cell biology studies as noted above and by the presence of multiple tRNA-related sequences and functions in the cis-acting replication signals on BMV RNAs (W. De Jong and P. G. Ahlquist, supra, 1995; M. Restrepo-Hartwig and P. Ahlquist, supra, 1996; R. Quadt, et al., supra, 1993; P. Ahlquist, supra, 1992; M. Sullivan and P. Ahlquist, *Sem. Virol.* 8:221-230, 1997).

Yeast expressing 1a and 2a from DNA plasmids replicate RNA3 or RNA3 derivatives and synthesize subgenomic mRNAs to express the coat gene or other genes substituted for it. Replicatable RNA3 derivatives can be introduced into yeast by transfection of in vitro transcripts (M. Janda and P. Ahlquist, *Cell* 72:961-970, 1993) or by in vivo transcription of an RNA3 cDNA flanked 5' by a DNA-dependent RNA polymerase promoter and 3' by a self-cleaving ribozyme (M. Ishikawa, et al., *J. Virol.* 71:7781-7790, 1997). Such cDNA-based RNA3 launching cassettes can be carried on yeast plasmids (M. Ishikawa, et al., supra, 1997) or, as shown here, integrated into a yeast chromosome. Expression of reporter genes substituted for the coat gene in RNA3 launching cassettes provides colony-selectable or -screenable markers for all forms of BMV RNA-dependent RNA synthesis, because such expression requires 1a-, 2a-directed negative-strand RNA synthesis, and subgenomic mRNA synthesis, and is strongly reduced if RNA-dependent positive-strand RNA amplification is blocked (M. Janda and P. Ahlquist, supra, 1993; M. Ishikawa, et al., supra, 1997).

The invention described below depends on the inventors' new understanding of yeast host genes required for viral replication. This information was obtained using the above-described BMV expression system and is described in detail below. Needed in the art of antiviral techniques is a method of preventing viral replication involving knowledge of essential host genes.

BRIEF SUMMARY OF THE INVENTION

In one embodiment, the present invention is an antiviral agent comprising an altered MAB1 gene, MAB2 gene, MAB3 gene, OLE1 gene, gene homolog or related gene. The agent is capable of inhibiting viral replication in a host cell.

In a preferred embodiment of the present invention, the host cell is a microbe or a eukaryotic cell. In a most preferred embodiment of the present invention, the host cell is a plant, animal, or yeast cell.

In another form, the present invention is a method of creating a virus-resistant organism comprising creating a transgenic organism containing an antiviral agent selected from the group of an altered MAB1 gene, MAB2 gene, MAB3 gene, OLE1 gene, homologs of these genes, related genes, and combinations of these genes and homologs.

The present invention also includes a method of creating a virus-resistant organism comprising creating a transgenic organism comprising an antiviral agent selected from the group of antisense sequences or sense sequences designed to alter the expression of MAB1, MAB2, MAB3 gene or OLE1 gene expression or MAB1, MAB2, MAB3 or OLE1 gene homologs or genes related to MAB1, MAB2, MAB3 or OLE1.

Figure 12:
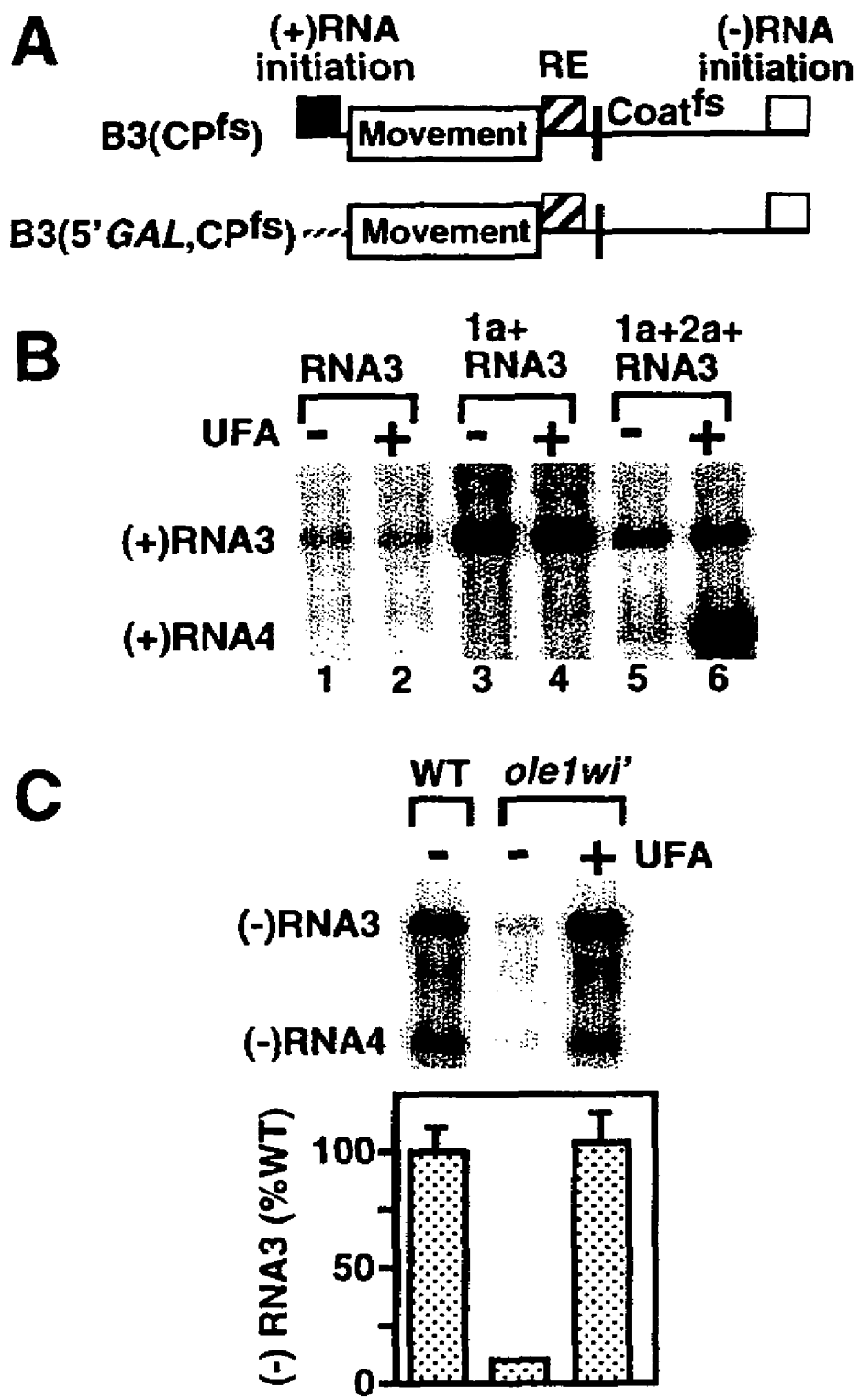

The present invention is also a method of increasing or optimizing replication of a virus or virus derivative by expression of MAB1, MAB2, MAB3 or OLE1 or a related or homolog gene from the same or different cell type, or combinations of such genes, or expression of modified versions of such genes, or alteration of the natural expression levels of such genes, to optimize the replication of the virus or derivative.

In a preferred form of the above-described method, the viral derivative is an expression vector derivative, the viral replication is within a plant or animal cell, or the viral replication is within a microbial cell.

It is an object of the present invention to provide antiviral agents and create transgenic virus-resistant organisms comprising these agents.

Other objects, advantages and features of the present invention will become apparent after one of skill in the art reviews the specification, claims and drawings.

BRIEF DESCRIPTION OF THE SEVERAL VIEWS OF THE DRAWINGS

FIG. 1 summarizes the identification of the MAB1 gene. FIG. 1A diagrams subcloning of complementing plasmid p1012. FIG. 1B graphs BMV-directed CAT expression in mab1-1 and YMI04 yeast expressing 1a and 2a and transfected with B3CAT and luciferase mRNA in vitro transcripts.

FIG. 2 is a Northern blot analysis of BMV RNA3 and RNA 4 accumulation in wild-type YPH500 yeast and mab1i yeast in the presence and absence of a plasmid containing the wild-type MAB1 gene.

FIG. 3A is a Western blot of HA-tagged Mab1p. FIG. 3B is an alignment of the predicted Mab1p sequence with selected additional proteins of the Sm family. The amino acid sequences of Sm motif1 and Sm motif2 from *Saccharomyces cerevisiae B* are provided in the sequence listing as SEQ ID NO:1 and SEQ ID NO:2, respectively: the amino acid sequences of Sm motif1 and Sm motif2 from *Saccharomyces cerevisiae D*1 are provided in the sequence listing as SEQ ID NO:3 and SEQ ID NO:4, respectively; the amino acid sequences of Sm motif1 and Sm motif 2 from *Saccharomyces cerevisiae E* are provided in the sequence listing as SEQ ID NO:5 and SEQ ID NO:6, respectively; the amino acid sequences of Sm motif1 and Sm motif2 from *Saccharomyces cerevisiae F* are provided in the sequence listing as SEQ ID NO:7 and SEQ ID NO:8, respectively; the amino acid sequences of Sm motif1 and Sm motif2 from *Saccharomyces cerevisiae G* are provided in the sequence listing as SEQ ID NO:9 and SEQ ID NO:10, respectively; the amino acid sequences of Sm motif1 and Sm motif2 from *Saccharomyces cerevisiae* MAB1 are provided in the sequence listing as SEQ ID NO:11 and SEQ ID NO:12, respectively; the amino acid sequences of Sm motif1 and Sm motif2 from *Schizosaccharomyces pombe* Z95620 are provided in the sequence listing as SEQ ID NO:13 and SEQ ID NO:14, respectively; the amino acid sequences of Sm motif1 and Sm motif2 from human Sm-Ca are provided in the sequence listing as SEQ ID NO:15 and SEQ ID NO:16, respectively; the amino acid sequences of Sm motif1 and Sm motif2 from *Caenorhabditis elegans* Z69302 are provided in the sequence listing as SEQ ID NO:17 and SEQ ID NO:18, respectively; the amino acid sequences of Sm motif1 and Sm motif2 from *Saccharomyces cerevisiae* MAK31 are provided in the sequence listing as SEQ ID NO:19 and SEQ ID NO:20, respectively; and the amino acid sequences of the conserved Sm motif1 and Sm motif2 are provided in the sequence listing as SEQ ID NO:21 and SEQ ID NO:22, respectively.

FIG. 4 is a comparison of Northern and Western blots showing accumulation of 1a and 2a mRNA and protein in wild-type YPH500 and mab1i yeast.

FIG. 5 demonstrates 2a mRNA half-life analysis. FIG. 5A shows wild-type YPH500 and mab1i yeast expressing 2a mRNA alone or in combination with 1a. FIG. 5B shows 2a mRNA levels from the experiment in FIG. 5A and similar experiments measured with a Molecular Dynamics Phosphorimager, expressed as a percentage of the t=0 RNA sample from wild-type YPH500 yeast lacking 1a, and plotted on a semilogarithmic plot vs. time.

FIG. 6A diagrams a pathway for initiating BMV-directed, RNA-dependent RNA replication and subgenomic mRNA synthesis from DNA. FIG. 6B is a bar graph describing BMV-directed GUS expression in wt YM104 and mutant ole1w yeast. FIG. 6C is a bar graph describing BMV-directed CAT expression in wt YM104 and mutant ole1w yeast transfected with B3CAT in vitro transcripts.

FIG. 7A is a schematic of a 5 kb region of yeast chromosome VII containing the OLE1 ORF, showing 2.9 kb fragment I that complements BMV-directed GUS expression in ole1w yeast and non-complementing fragments II and III. FIG. 7B is a bar graph demonstrating complementation of BMV-directed GUS expression in ole1w yeast by fragment I of panel A. FIG. 7C is a bar graph demonstrating that isogenic strain, ole1w, constructed by replacing the OLE1 gene in wt YMI04 with the ole1w gene from mutant yeast, reproduced the phenotype of the original ole1w mutant.

FIG. 8A is a schematic of the pathway of unsaturated fatty acid synthesis and incorporation into membrane phospholipids. FIG. 8B is a bar graph demonstrating that UFAs restore BMV-directed GUS expression in OLE1-deleted yeast (ole1Δ::URA3) and ole1w yeast.

FIG. 9A is a western blot analysis of 1a and 2a protein accumulation in wt and ole1w yeast containing a plasmid expressing B3CAT and either ADH1-promoted 1a and 2a expression plasmids (lanes 1-3) or GAL1-promoted 1a and 2a expression plasmids (lanes 4-6). FIG. 9B is a bar graph demonstrating BMV-directed CAT expression in the yeast cells described in panel A. FIG. 9C demonstrates distribution of 1a and 2a between membrane and soluble cytoplasmic fractions in ole1w yeast with or without the UFA supplementation.

FIG. 10 is a northern blot analysis of RNA3 and RNA4 accumulation in wt and ole1w yeast containing plasmids directing GAL1-promoted expression of 1a, 2a and the indicated RNA3 derivatives.

FIG. 11 is a northern blot analysis of BMV-positive-strand RNA3 accumulation in ole1w yeast expressing the indicated BMV components.

FIG. 12 demonstrates inhibition of negative-strand RNA3 synthesis in ole1w yeast. FIG. 12A is a schematic of B3(5'GAL, CP$^{fs}$) and its parent B3CP$^{fs}$, indicating cis-acting elements required for template recruitment (RE), negative-strand initiation and positive-strand initiation. FIG. 12B is a northern blot analysis of positive-strand RNA3 accumulation in wt and ole1w yeast expressing the indicated BMV components. FIG. 12C is a northern blot analysis of negative-strand RNA3 accumulation in wt and ole1w yeast expressing 1a, 2a and B3(5'GAL, CP$^{fs}$).

DETAILED DESCRIPTION OF THE INVENTION

A. In General

In one embodiment, the present invention is directed towards antiviral agents developed from the observation that four particular yeast genes (MAB1, MAB2, MAB3 and OLE1), have been found by the inventors to affect viral replication. By "antiviral" we mean inhibitory to RNA viruses, preferably positive strand. In another embodiment, the invention is inhibitory to double-stranded RNA viruses.

In the Examples below, we describe specific yeast genes whose mutation was found to inhibit brome mosaic virus (BMV) replication, identification of the MAB1, MAB2, MAB3 and OLE1 genes by their ability to restore BMV-directed RNA replication and expression in the mutants, and characterization of these yeast genes and yeast genes products. We inventors also describe a proposed use of the MAB1, MAB2, MAB3 and OLE1 genes (or homologs or related genes) to develop antiviral agents and vector systems.

The antiviral uses of the present invention include constructing a transgenic organism containing an altered MAB1, MAB2, MAB3 or OLE1 gene or containing antisense nucleic acids designed to alter the native function of the MAB1, MAB2, MAB3 or OLE1.

B. Evaluation of Altered Genes

By "altered gene" is meant mutated, enhanced, synthetic, or duplicated MAB1, MAB2, MAB3 or OLE1 genes (including some or all of the coding, non-coding, regulatory, and promoter regions that inhibit viral replication). The inventors envision that the particular gene mutations that they studied are not the only mutations of the MAB1, MAB2, MAB3 and OLE1 that would result in analogous antiviral activity. Thus, the present invention encompasses any mutation or alteration of MAB1, MAB2, MAB3 or OLE1 that results in significant alteration of viral replication. This mutation may result in the absence of gene expression or in the expression of an altered product.

One would obtain an altered gene by mutagenizing or altering a wild-type MAB1, MAB2, MAB3 or OLE1 gene. To obtain a wild-type MAB1, MAB2, MAB3 or OLE1 gene, one would most typically examine the nucleotide sequences of the gene (see Table 1, below, for reference to the yeast protein database and GenBank Accession Number and obtain primers sufficient to amplify the gene from a yeast genomic library. (GenBank Accession Nos. Z49399, U32517, Z71340 and Z72577 are incorporated by reference as if set forth entirely herein.) Of course, other methods would be known to one of skill in the art.

To mutagenize or alter the gene, one would look below to the Examples for one method of creating altered genes. Of course, other methods are known to those of skill in the art, including those described in Umen and Guthrie, *Genetics* 143:723-739, 1996, incorporated by reference herein.

One would test the candidate altered gene by methods described in the sections below. For example, one might test a candidate altered gene by use of a virus-directed reporter gene expression system, as exemplified below with BMV.

One would also be able to construct RNA-mediated interference agents, such as an antisense, sense or double-stranded transcript designed to inhibit or alter gene function (See Fire, et al., *Nature* 391:806-811, 1998, *Nature* 391:744-745, 1998; Bingham, et al., *Cell* 90:385-387, 1997, all incorporated by reference as if fully set forth herein).

Additionally, the inventors envision that virus replication can be inhibited by decreasing or increasing the expression of the gene (MAB1, MAB2, MAB3 or OLE1 or combinations of such genes), expressing a related gene or gene homologs from the same or a different cell type, or altering the natural copy or copy number of the gene or combinations of such genes. One might also express altered versions of the gene, or of related gene or genes from the same or a different cell type, or combinations of such altered genes in addition to the natural copy of the gene.

The inventors envision expressing derivatives of the gene or of a related gene or genes from the same or a different cell type, such as partial segments of the gene or fusions of the entire gene or segments thereof to other protein domains.

A preferred altered gene of the present invention is a dominant negative mutation of MAB1, MAB2, MAB3, OLE1 or related genes or homologs. One would characterize such a mutation by the ability of the mutation to shut down viral replication once the mutated gene is present in the host organism, even when the wild-type gene is also present in the organism. One of skill in the art would develop these mutations by generally known procedures. For example, one would review Herskowitz, I., et al., *Nature* 329:219-222, 1987 as a reference for mutations of cellular genes, Baltimore, D., et al., *Nature* 335:395-397, 1998 for viral genes, and Holzmayer, et al., *Nucl. Acid. Res.* 20:711-717, 1992 for lambda bacteriophage, and Brachmann, et al., *Proc. Natl. Acad. Sci. USA* 93:4091-4095, 1996 for dominant negative mutations of p53 selected in yeast.

C. Homologs and Related Genes

The inventors also envision that there are homologs to MAB1, MAB2, MAB3 and OLE1 in other organisms. For example, the inventors are aware that LSM/MAB1 and a related set of interacting LSM proteins are conserved from yeast to humans (Schweinfest, et al., *Canc. Res.* 57:2961-2965, 1997; Salgado-Garrido, et al., *EMBO J.* 18:3451-3462, 1999; Achsel, et al., *EMBO J.* 18:5789-5802, 1999). A "homolog" is defined herein as a gene, preferably from another species, with a sufficient sequence or functional similarity to MAB1, MAB2, MAB3 or OLE1 such that the homolog functions in a similar manner in the non-yeast species. The inventors also envision that there may be homologs of MAB1, MAB2, MAB3 and OLE1 present in yeast species. Such genes can be identified by sequence similarity or by functional screens.

With regard to OLE1, the inventors note that Δ9 fatty acid desaturase (the function encoded by OLE1 in yeast) is also the rate-limiting, initial enzyme for UFA synthesis in animals (J. M. Ntambi, *J. Lipid Res.* 40:1549-1558, 1999).

The inventors also envision that the manipulation of genes related to MAB1, MAB2, MAB3 and OLE1 could alter viral expression. By "related gene" is meant an associated gene. For example, MAB1, MAB2, MAB3 or OLE1 may be part of a functional complex and the alteration of a complex member may prove effective to alter viral replication. In one example, MAB3 is identified below as a member of a chaperone complex, involving many cofactors. These other cofactors may also be candidates for antiviral agents. (See Hu, et al., *EMBO*

J. 16:59-68, 1997 for a discussion of Hepadnavirus involvement in the chaperone complex.)

D. Host Organisms

The inventors envision that the present invention will be useful in a variety of organisms, most particularly plants, human, microbe and animal cells.

E. Use of Antiviral Agents of the Present Invention

The present invention is therefore an antiviral agent comprising an altered MAB1, MAB2, MAB3 or OLE1 gene or homologs of these genes, or related genes, or combinations of these genes, wherein the agent is capable of altering viral replication in a host cell. In one embodiment, the altered gene or gene homolog is a mutated gene. In another embodiment, the altered gene is a naturally occurring gene and the host cell contains an antisense or sense transcript capable of altering gene expression.

In a preferred embodiment, the invention is directed to increasing or optimizing replication of a virus or virus derivatives by expression of the gene (MAB1, MAB2, MAB3, OLE1), a related or homolog gene from the same or a different cell type, or combinations of such genes, or expression of modified versions of such genes, or alteration of the natural expression levels of such genes, to optimize the replication of a virus or its derivatives, including expression vector derivatives, in any of the various cell types described above. To use the antiviral agents of the present invention, one might use a variety of molecular biological methods. For example, one might construct a transgenic plant cell with a altered gene corresponding to a homolog of MAB1, MAB2, MAB3 or OLE1. One would expect that this plant cell would be not capable of supporting viral replication and, when regenerated into a mature plant, would provide a virus-resistant plant.

Similarly, other transgenic viral-resistant organisms may be created through standard techniques known to those of skill in the art of molecular biology.

One could most easily determine whether an organism is virus-resistant by challenging the organism with a test virus and evaluating viral replication relative to a control challenge.

F. Use of Genes as Argets for Antiviral Screens

We envision that the MAB1, MAB2, MAB3 or OLE1 gene, regulatory sequences and regulatory factors and encoded proteins are appropriate targets for antiviral drug discovery. Such discovery can be pursued by any of a number of in vivo or in vitro methods well-known to those in the art, such as screening libraries of chemical compounds for effects on the expression, stability and activity of the OLE1 protein. Procedures to assay for gene expression, protein levels and enzyme activity are well-known in the field. Among these are, e.g., nucleic acid hybridization- and reverse transcription/PCR-based methods for assaying specific mRNA levels, and ELISA and other assays for specific protein levels. Assays for enzyme activities such as the Δ9 fatty acid desaturase activity of OLE1 could be based on a variety of detection approaches, such as the incorporation or release of a chemical group assayable by fluorescence, light absorbance, radioactivity, etc.; a conformational change in a reaction product relative to a reaction substrate, leading to changes in fluorescence, light absorption or other property, etc.; and many other approaches known to those in the art. We specifically envision Δ9 fatty acid desaturase genes and gene products in other organisms as targets for antiviral drug discovery, as described above.

In one embodiment, the present invention is a method of evaluating a substance as an antiviral therapy, comprising the steps of (a) exposing a substance to a protein selected from the group consisting of the MAB1, MAB2, MAB3 or OLE1 expression products, and (b) evaluating the effect of the substance on the stability or activity of the protein expression product, wherein the inhibition of the activity or stability expression product indicates that the substance is a possible antiviral therapy. Screens for compounds that inhibit enzyme activity would likely be conducted with extracts of cells rather than purified protein and might also be conducted with whole cells. For example, using OLE1 as an example, screens for compounds selectively affecting OLE1 protein stability would preferably be conduced in cells or animals. Selective effects on OLE1 protein (Ole1p) stability would likely result from the effects of a compound on the complex in vivo systems affecting Ole1p intracellular localization and on systems like ubiquitin ligase, the proteasome, etc. that affect protein degradation.

In another embodiment, the present invention is a method of evaluating a substance as antiviral therapy, comprising the step of (a) exposing the substance to a protein expression system, such as whole cells in culture or a purified transcription or protein expression system, wherein the system expresses a protein selected from the group consisting of MAB1, MAB2, MAB3 or OLE1 expression products, and (b) evaluating the effect of the substance on the expression level of the expression product, wherein the inhibition of the expression level indicates that the substance is a possible antiviral therapy.

Screens for compounds that induce changes in gene expression and protein expression most likely would be conducted using cells in culture, not purified transcription or protein expression systems. Such tests would eventually also be conducted in whole animals. Using OLE1 as an example, selective changes in OLE1 transcription, e.g., might be inducible by a drug because OLE1 expression is regulated by extracellular levels of some lipids and related products. Such lipids likely bind to one or more cell surface receptors that in turn send specific signals to the nucleus to alter OLE1 transcription. The candidate drug might interact with this cell surface receptor (or a downstream factor in the signal transduction pathway) to induce selective effects on OLE1 transcriptional regulation. In a preferred form of the invention, we would employ a cell culture system because in a simplified in vitro transcription system, it is less likely that we could find selective inhibitory effects on OLE1 transcription without inducing general transcription inhibition.

In another embodiment, the invention is a method of evaluating a substance as an antiviral therapy, comprising the step of (a) exposing a substance to a transcription system, wherein the system transcribes an mRNA product selected from the group consisting of MAB1, MAB2, MAB3 or OLE1 mRNAs, and (b) evaluating the effect of the substance on the expression level or stability of the mRNA product, wherein the inhibition of the expression level or decrease in stability indicates that the substance is a possible antiviral therapy. As discussed above, we envision that a preferable system will be a whole cell or cell extract system rather than a purified transcription system.

In another embodiment, the present invention is the above-identified screens for protein activity, expression and stability, and mRNA expression and stability for the enzyme encoded by OLE1, Δ9 fatty acid desaturase. Applicants note that this enzyme name is generally applied to the class of homologous enzymes from yeast and other cells. There is much homology and functional equivalents among such genes. It is known that the human protein can functionally replace the yeast protein. By the "A9 fatty acid desaturase" we mean to include all homologs of this enzyme and specifically note that mammalian organisms are known to contain several homologs. By "homolog" we mean to include enzymes that are functionally equivalent to the OLE1-encoded enzyme.

EXAMPLES

A. Mutations in multiple yeast complementation groups inhibit brome mosaic virus RNA replication and transcription and perturb regulated expression of the viral polymerase-like gene.

1. In General

Brome mosaic virus (BMV), a member of the alphavirus-like superfamily of positive-strand RNA viruses, encodes two proteins, 1a and 2a, that interact with each other, with unidentified host proteins, and with host membranes to form the viral RNA replication complex. Yeast expressing 1a and 2a support replication and subgenomic mRNA synthesis by BMV RNA3 derivatives. Using a multistep selection and screening process, we have isolated yeast mutants in multiple complementation groups that inhibit BMV-directed gene expression. Three complementation groups, represented by mutants mab1-1, mab2-1 and mab3-1 (for maintenance of BMV functions), were selected for initial study. Each of these mab mutants has a single, recessive, chromosomal mutation that inhibits accumulation of BMV positive-strand and negative-strand RNA3 and subgenomic mRNA. BMV-directed gene expression was inhibited when the replication template was introduced by in vivo transcription from DNA or by transfection of yeast with in vitro transcripts, confirming that cytoplasmic replication steps are defective.

mab1-1, mab2-1 and mab3-1 slowed yeast division to varying degrees and showed temperature sensitive restriction of growth, implying that the affected genes contribute to normal cell growth. In wild-type yeast, expression of the helicase-like 1a protein increased the levels of 2a mRNA and the polymerase-like 2a protein. In association with their other effects, mab1-1 and mab2-1 block the ability of 1a to stimulate 2a mRNA and protein accumulation. mab3-1, however, shows elevated 2a protein accumulation. Since mab3-1 is recessive and does not elevate 2a mRNA levels, this suggests that MAB3 both supports BMV RNA replication and contributes to degradation of at least some pools of 2a. Together, these results show that BMV RNA replication in yeast depends on multiple host genes, some of which directly or indirectly affect the regulated expression, accumulation and turnover of 2a, possibly in connection with replication complex assembly.

2. Isolation of *S. cerevisiae* Mutants in which BMV RNA Replication is Reduced.

We have previously constructed plasmids from which BMV RNA3 derivatives can be transcribed in vivo from the galactose-inducible yeast GAL1 promoter and terminated by a self-cleaving ribozyme at or near their natural 3' end. (See M. Ishikawa, et al., *J. Virol.* 71(10):7781-7790, 1997, herein incorporated by reference.) Upon induction with galactose, yeast harboring such plasmids transcribed and accumulated BMV RNA3 derivatives but failed to express the gene placed in the coat protein (CP) position because the CP gene is located downstream of the 3a gene. In contrast, in yeast expressing the 1a and 2a proteins, GAL1 promoter-driven BMV RNA3 derivative RNAs are subjected to RNA-dependent RNA replication and subgenomic RNA4 transcription to express the gene placed in the CP gene position. In the system, the expression of the gene was shown to be dependent on both BMV RNA3 replication steps and subgenomic RNA4 synthesis. By using this system, we designed a screening strategy to select cells which express less efficiently the gene placed in the CP gene position to isolate mutant yeast with reduced BMV RNA replication, stability, or expression.

B3URA3 and B3GUS are BMV RNA3 derivatives with the CP gene replaced with the yeast uracil biosynthesis gene URA3 and *E. coli* β-glucuronidase (GUS) gene, respectively. The yeast strain YMI04 is a YPH500 derivative harboring two gene cassettes, [GAL1 promoter-B3URA3-ribozyme] and [GAL1 promoter-B3GUS-ribozyme], integrated in the chromosomal can1 and lys2 loci, respectively. In addition, YMI04 has pB1CT19 and pB2CT15, yeast 2μ plasmids carrying constitutive ADH1 promoter-driven BMV replication proteins 1a and 2a gene cassettes, respectively. YMI04 was [Ura+ Gus+] if cells were grown in galactose medium, and [Ura− Gus−] if cells were grown in glucose medium or either 1a or 2a plasmids was lost. In keeping with the Ura+ phenotype, YMI04 showed 1%-5% of plating efficiency on a 5-fluoro-orotic acid (5-FOA)-containing galactose plate lacking His and Leu (omission of His and Leu was necessary to maintain 1a and 2a expression plasmids) compared to that on a corresponding plate without 5-FOA. By filter-lift assay using X-gluc, YMI04 cells grown in galactose medium developed detectable blue color within 20-30 minute incubation at 37° C. In contrast, a lys2::B3Gus strain lacking 1a or 2a plasmids developed no detectable blue color even after 24 hour incubation. Total protein extracts from YMI04 cells grown in galactose medium showed. GUS activity of approximately 20-50 nmol 4 MU/mg protein/m in.

We mutagenized YMI04 by ultraviolet irradiation, and after overnight growth on glucose plates lacking His and Leu, cells were harvested and plated on 5-FOA galactose plates lacking His and Leu to select mutants with reduced BMV-directed URA3 expression. From $1.6 \times 10^5$ viable cells plated, approximately 2,000 colonies that appeared between 5-7 day incubation were picked and streaked on galactose plates lacking His and Leu. Gus activity expressed in these cells was estimated by filter-lift/X-gluc assay, and 34 cells which showed slow or no blue color development were selected.

To distinguish between mutations in BMV components (1a, 2a, B3URA3 or B3GUS) and host genes, these 34 mutant candidates were mated with YMI06, a YPH499 derivative with LYS2+genotype, and diploids were generated. The resulting diploids were grown on galactose plates, and assayed for Gus activity by filter-lift assay. Among the mutant 34 candidates, 7 strains recovered Gus activity, suggesting that each of these 7 strains carried a recessive mutation that can be complemented by the yeast genome supplied by YMI06, i.e., recessive mutation on the yeast chromosome. The other 27 strains recovered Gus activity by mating with YMI06 with either active BMV 1a or 2a expression plasmids, suggesting that these 27 strains carried recessive defects in 1a or 2a genes. We selected four strains, designated #1-33, #16-10, #4-29 and #1-20 (note: mab1-4) from the 7 mutant candidates and analyzed further.

We first examined how severely the BMV-directed Gus expression was reduced in these strains quantitatively. The strains were cultured in galactose liquid medium for two days, harvested, disrupted, and the Gus activity in the resulting cell extract was measured. Gus activity for these strains ranged from 1% to 5% levels of the parental wild-type strain, YMI04. In contrast, diploids generated by mating between the strains and YMI06 showed Gus activity ranging from 50% to 90% levels of wild-type diploids generated by mating between YMI04 and YM106. These results confirmed filter-lift assay results. In wild-type diploid cells (YMI04×YMI06), the levels of Gus activity were approximately one-fifth of those in haploid YMI04. At present, we do not know why less Gus activity is expressed in diploid cells.

The growth of #16-10, #4-29 and #1-20 at 28° C. was slower than that of the parental strain YMI04. At 37° C., #1-33, #16-10 and #4-29 showed growth defect, and #1-20 showed growth defect at 15° C. Diploid strains generated by the crosses between these four strains and wild-type yeast did not show slow growth at 28° C. or growth defect at extreme conditions, suggesting that the growth phenotypes are controlled by recessive traits.

3. Each Mutant Had a Single Recessive Chromosomal Mutation Belonging to a Distinct Complementation Group.

To characterize the genetic traits controlling the phenotype of reduced Gus activity, we sporulated diploids generated by mating #1-33, #16-10, #4-29 or #1-20 and YMI08 derivatives with lys2::[GAL1 promoter-B3GUS ribozyme] integration, dissected more than 20 tetrads for each strain, supplemented 1a and/or 2a expression plasmids if necessary, grew in galactose medium, and measured Gus activity. The tetrad analysis was consistent with each mutant strain carrying a single mutation that interfered with BMV-directed GUS expression. In addition, evidence was found for some modifier locus differences between the starting parents YMI04 and YMI08. Crosses between the mutants showed that each was in a different complementation group.

B. Characterization of MAB1, MAB2 and MAB3 Genes
  1. In General

Brome mosaic virus (BMV) is a member of the alphavirus-like superfamily of positive-strand RNA viruses of animals and plants. Yeast expressing BMV RNA replication proteins 1a and 2a support the replication of BMV RNA3 derivatives. We describe above the isolation of yeast strains with mutations designated mab1-1, mab2-1 and mab3-1, which inhibit BMV RNA replication and subgenomic mRNA synthesis. In this section, we describe the identification of the MAB1, MAB2 and MAB3 genes by their ability to restore BMV-directed RNA replication and gene expression in the mutants.

Three reports from the Yeast Protein Database are summarized below in Table 1 and describe the yeast genes corresponding to the mab1-1, mab2-1, and mab3-1 mutations.

In brief, we found that MAB1 encodes a 20 kDa protein containing both Sm motifs that are conserved in the core Sm proteins of snRNPs and have been suggested to be involved in protein-protein interaction. MAB2 encodes an 88 kDa protein containing similarity to the WD-40 repeat, which is found in proteins involved in signal transduction, RNA processing, and membrane vesicle traffic, and has also been suggested to participate in protein-protein interaction. MAB2 is essential for yeast growth at 30° C., while MAB1 is dispensable at 30° C. but essential at 37° C. MAB3 encodes a 409 amino acid protein with a molecular weight of approximately 44.6 kDa. The protein is present in the cytoplasm and on the endoplasmic reticulum and nuclear envelope.

Overall, the results suggest that these host genes are required for the assembly and/or function of the BMV RNA replication complex.

2. Cloning of Yeast Genomic DNA Fragments Complementing MAB1, 2 and 3 Mutations.

Isolation of the MAB1 gene. Starting from yeast strain YMI04, we previously isolated mutant yeast strains defective in supporting brome mosaic virus (BMV) RNA replication and subgenomic mRNA synthesis (M. Ishikawa, et al., supra, 1997). YMI04 is a YPH500 derivative containing 2μ DNA plasmids expressing BMV RNA replication proteins 1a and 2a and chromosomally-integrated cDNA cassettes from which replicatable BMV RNA3 derivatives B3URA3 and B3GUS are transcribed from the galactose-inducible, glucose-repressible GAL1 promoter. In these cells, the B3URA3 and B3GUS RNAs are replicated and direct synthesis of subgenomic mRNAs that express the URA3 and GUS genes, respectively. These yeast were mutagenized with ultraviolet light and subjected to a multistep selection and screening process to isolate mutant yeast strains in which BMV-directed gene expression was inhibited. One of these yeast mutants, mab1-1, was found to have a single, recessive, chromosomal mutation that inhibits BMV-directed RNA3 replication and subgenomic mRNA synthesis, and produces temperature-sensitive inhibition of yeast growth at 36° C. (M. Ishikawa, et al., supra, 1997).

To identify the responsible mutant gene, we transformed mab1-1 yeast with a yeast genomic DNA library constructed in Ycp50, a centromeric vector carrying URA3 as a selectable marker (Rose, Gene, 60(2-3):237-243, 1987). The transformed cells were plated on minimal glucose plates lacking uracil, incubated 12 hours at 24° C., and then transferred to 36° C. to screen for clones in which the growth defect at 36° C. was rescued. From each of four transformants that grew at 36° C., the library plasmid was recovered and amplified in *E. coli*. Restriction mapping showed that all four plasmids contained distinct but overlapping yeast DNA fragments.

TABLE 1

|  | MAB1 | MAB2 | MAB3 | OLE1 |
| --- | --- | --- | --- | --- |
| SGD (*Saccaromyces* Genome Database) Systemic gene name | YJL124C | YDR324C | YNL064C | YGL055W |
| GenBank Accession no. | Z49399 | U32517 | Z71340 | Z72577 |
| Synonyms | LSM1/SPB8/ J0714 | D9798.12 | YDJ1/MAS5/ N2418/ YNL1614/ YNL2418 | OLE1/MDM2/ G3472 |
| Yeast chromosome | X | IV | XIV | VII |
| Predicted length (amino acids) | 172 | 776 | 406 | 510 |
| Predicted protein molecular weight | 20304 | 87793 | 44379 | 58411 |
| Predicted protein isolectric point | 5.840 | 6.370 | 6.270 | 9.12 |

One of these plasmids, designated p1012, was introduced into mab1-1 yeast and tested again for complementation of the defects in growth at 36° C. and in BMV-directed GUS expression via B3GUS RNA replication and subgenomic mRNA synthesis. FIG. 1 summarizes the identification of the MAB1 gene. FIG. 1A diagrams subcloning of complementing plasmid p1012. The solid bars indicate DNA fragments that complement the mutation. The GUS values represent the percentage of GUS expression relative to wild-type YMI04 yeast. FIG. 1B graphs BMV-directed CAT expression in mab1-1 and YMI04 yeast expressing 1a and 2a and transfected with B3CAT and luciferase mRNA in vitro transcripts. After transfection, cells were incubated in glucose medium and assayed for luciferase and CAT activity after 5 hours and 21 hours, respectively. Luciferase mRNA (transcribed from pGEM-luc, Promega) was cotransfected as an internal standard because its translation is independent of BMV-directed RNA synthesis. Thus, in each sample CAT activity was normalized to luciferase activity to control possible variation in transfection efficiency. No strain-specific variation was observed in luciferase expression. Averages and standard deviations from 3 independent experiments are shown.

As shown in FIG. 1A, p1012 complemented both phenotypes to wild-type levels. p1012 also restored wild-type levels of BMV-directed CAT expression from in vitro transcripts of another RNA3 derivative, B3CAT, transfected into mab1-1 yeast (FIG. 1A). This confirms that mab1-1 inhibition of BMV-directed gene expression is independent of the DNA-based launching of the B3URA3 and B3GUS RNA replicons. Similarly, p1012 and certain of its derivatives restored wild-type amplification of RNA3, the negative-strand RNA3 replication intermediate, and the wt subgenomic mRNA, RNA4, in mab1-1 yeast containing a plasmid expressing wild-type RNA3.

DNA sequencing showed that the yeast DNA insert of p1012 corresponded to a region of chromosome X containing multiple open reading frames (ORFs) (FIG. 1A). To identify which ORF was responsible for complementing mab1-1, a series of deletions was prepared from p1012, transformed into mab1-1 yeast and tested for complementation (FIG. 1A). The plasmid in this series with the smallest complementing DNA insert, p1195, contained two truncated ORFs and one complete ORF, denoted YJL124c by the yeast genome sequencing project. The same truncated ORFs were included in plasmids p1138 and p1141, respectively, which did not complement mab1-1, suggesting that complementation was a property of YJL124c.

To determine whether YJL124c corresponded to the wild-type locus of mab1-1 rather than an extragenic suppressor, URA3 was integrated next to wild-type YJL124c and the wild-type MAB1 phenotype was shown to co-segregate with URA3 after crossing this strain and with mab1-1 yeast. The 0.76-Kb EcoRV-ClaI fragment of the wild-type MAB1 gene was subcloned between the SmaI and ClaI sites of pRS306, a yeast integrating plasmid bearing URA3. The resultant plasmid was digested with EcoNI to direct its integration to YJL124c, transformed into the wild-type MATa strain YMIO8, and Ura+ transformants were selected. Integration of the plasmid at the intended site was verified by Southern analysis. The Ura+ transformants were crossed with the original mab1-1 mutant, the diploids were sporulated, and the meiotic products were tested for BMV-directed GUS activity, growth at 36° C., and growth on medium lacking uracil. All 24 tetrads analyzed were parental ditypes with 2 GUS+ Ts+ Ura+ spores and 2 GUS− Ts− Ura− spores, where GUS− reflected BMV-directed GUS expression averaging 10-fold lower than GUS+ spores. Based on this close linkage of mab1-1 complementation to YJL124c and the isogenic mutant results described below, YJL124c is referred to hereafter as MAB1.

Figure 3:
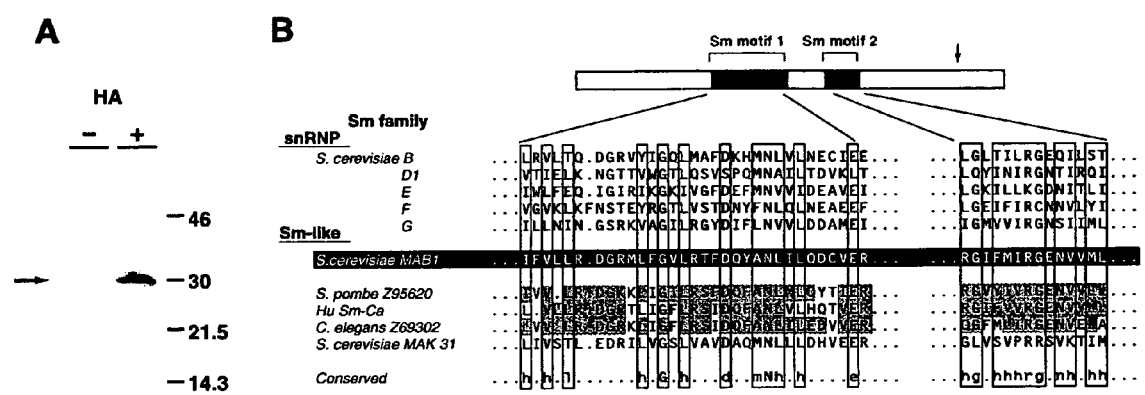

Mab1p contains similarities to core snRNP proteins. MAB1 encodes a putative protein of 172 amino acids. To test for expression of this predicted protein, a triple HA epitope tag was inserted at the N terminus of Mab1p. When introduced on a centromeric plasmid into mab1-1 yeast, the epitope-tagged MAB1 gene restored growth at 36° C. and restored BMV-directed GUS expression to wild-type levels. FIG. 3A is a Western blot of HA-tagged Mab1p. Total protein was extracted from YMI04 yeast containing plasmid pMAB1 or pMAB1-HA, respectively, electrophoresed on a 15% polyacrylamide SDS gel, transferred to membrane, incubated with an anti-HA monoclonal antibody (Boehringer) and visualized by chemiluminescence. FIG. 3B is an alignment of the predicted Mab1p sequence with selected additional proteins of the Sm family. The boxes highlight residues conserved among Sm motifs. The arrow above the MAB1 ORF map at top indicates the location of the mab1-1 frameshift mutation. Protein sequence comparisons were performed using the BLAST algorithm, accessed via the National Center for Bioinformatics. Occasional spaces were included to facilitate alignment. Color-highlighted regions of the *Schizosaccharomyces pombe* Z95620, human Ca—Sm, and *Caenorhabditis elegans* Z69302 sequences indicate amino acids identical or similar to the corresponding position in Mab1p. In the consensus sequence, upper-case letters correspond to residues that are absolutely conserved while lower-case letters correspond to residues conserved in at least ⅔ of the sequences analyzed. h indicates that a hydrophobic residue is present in at least ⅔ of the sequences. This analysis is based on Fromont-Racine, *Nature Genetics* 16:277-282, 1997; Hermann, *EMBO J.* 14:2076-2088, 1995; Seraphin, *EMBO J.* 14:2089-2098, 1995.

Western blot analysis demonstrated that an epitope tagged protein near the anticipated size was expressed (FIG. 3A).

Mab1p contains regions similar to the two Sm motifs, which are conserved among the eight common or core proteins of the small nuclear ribonucleoprotein particles (snRNPs) that assemble to form the spliceosome directing pre-mRNA splicing (FIG. 3B). Sm motifs are also found in other proteins not known to be associated with splicing, such as the yeast MAK31 protein, the human Sm—Ca protein, and other proteins of unknown functions (Hermann, *EMBO J.* 14:2076-2088, 1995; Seraphin, *EMBO J.* 2089-2098, 1995). Intriguingly, Mak31p is required for maintenance of an endogenous, virus-like dsRNA element in yeast. BLAST analysis showed that Mab1p shares more extensive similarity, including its complete C-terminal half, with a putative protein from *Schizosaccharomyces pombe* (43% identity, 68% similarity) and a human protein, CaSm, involved in maintaining the transformed state of pancreatic cancer cells and showing elevated expression in tumor cell lines from many tissues (45% identity, 68% similarity) (Schweinfest, *Cancer Res.* 57:2961-2965, 1997).

Mab1p has been suggested to be a possible U6 snRNP-associated protein from the Sm B family (Fromont-Racine, *Nat. Genet.* 16:277-282, 1997). However, to our knowledge, there is no experimental evidence to support this suggestion. Immunoprecipitation analysis of yeast Mak31p showed no association with snRNP RNAs, suggesting that some proteins bearing Sm motifs may not be snRNP-associated.

MAB1 is not essential for yeast growth at 30° C. To determine if MAB1 was required for cell growth, a mab1::URA3 disruption allele was constructed by replacing 58% of the MAB1 coding region with the URA3 gene. The resulting locus can express at most only the N-terminal 33 amino acids of the 172 amino acid Mab1p, while even a much shorter C-terminal truncation abolished Mab1p function (p1138 in FIG. 1A). To construct this disruption, a plasmid containing the mab1::URA3 allele was digested and used to disrupt one MAB1 allele of the diploid strain YJD00. The resulting MAB1/mab1::URA3 diploids were isolated on plates lacking uracil, and confirmed by Southern blot analysis. Two independent Ura$^+$ transformants were sporulated and tetrads were dissected. In all 84 tetrads examined, all four haploid progeny were viable at 30° C., growing at a nearly wild-type rate. At 36° C., all tetrads displayed a 2 Ura$^+$ Ts$^-$:2 Ura$^-$ Ts$^+$ segregation pattern. Thus, MAB1 is essential only at elevated temperatures. MAB1 disruption in haploid wild-type YPH500 was performed similarly, yielding the expected temperature-sensitive growth defect at 36° C. This strain was named mab1Δ.

Identification of the mab1-1 mutation and construction of a mab1-1 strain isogenic to YPH500. To identify the causal mutation, the mab1-1 allele was cloned by gap repair (Orr-Weaver, *Proc. Natl. Acad. Sci. USA* 78:6354-6358, 1981) and sequenced. Briefly, we generated two deletion derivatives of the MAB1 locus on TRP1-containing plasmids. These derivatives had deletions of the PstI/ClaI or ClaI/EcoNI fragments, which together encompass the MAB1 gene. These plasmids were independently transformed into mab1-1 yeast, resulting in recombination with the chromosomal mab1-1 allele to repair the gap and thus circularize the plasmid for replication. Such gap-repaired plasmids were recovered from Trp$^+$ transformants, amplified in *E. coli*, and retransformed into mab1-1 yeast to verify lack of complementation. Sequencing revealed a single change in the form of the deletion of one adenine from a run of 7 adenines at nucleotide position 463468 in the ORF. This frameshifted the ORF after amino acid 156, resulting in translation of an additional 68 amino acids from an alternate frame prior to termination.

To insure the absence of extraneous mutations such as might be present in the original UV-mutagenized mab1-1 strain, the mab1-1 point deletion was transferred into wild-type YPH500 yeast, the progenitor of YMI04. To obtain this strain, designated mab1i, mab1Δ yeast cells were transformed with a DNA fragment containing the mab1-1 allele, and plated on 0.1% 5-fluoroorotic acid, which selects against yeast expressing active URA3 and thus for cells in which the mab1::URA3 locus has been replaced by recombination with the mab1-1 DNA fragment. The resulting Ura– mab1i strain showed the expected temperature-sensitive growth phenotype.

Figure 2:
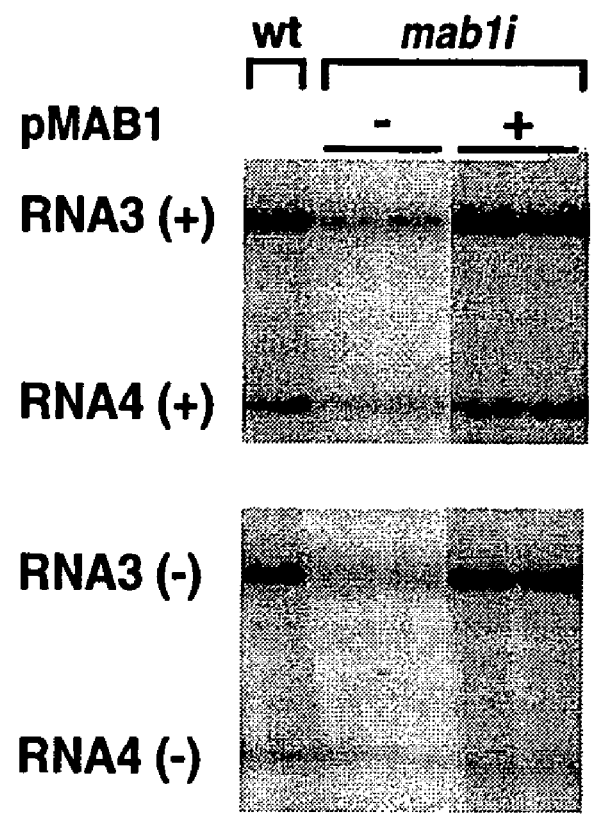

To compare BMV RNA replication and subgenomic mRNA synthesis in mab1i and mab1Δ yeast with the original mutant strain, mab1i and mab1Δ yeast were transformed with plasmids expressing 1a, 2a, and wild-type BMV RNA3. FIG. 2 is a Northern blot analysis of BMV RNA3 and RNA 4 accumulation in wild-type YPH500 yeast and mab1i yeast in the presence and absence of a plasmid containing the wild-type MAB1 gene. Total RNA was extracted and loaded on a denaturing 1% agarose-formaldehyde gel, transferred to nylon membrane and probed for BMV RNA3 and RNA4.

Northern blot analysis (FIG. 2) revealed a close parallel between mab1i, mab1Δ and mab1-1 yeast in their inhibition of positive- and negative-strand RNA3 and RNA4 accumulation relative to wild-type yeast, and in the restoration of accumulation of these RNA replication products upon introduction of p1195, which contains wild-type MAB1. Similarly, transformation of mab1i and mab1 yeast with plasmids expressing 1a, 2a, and B3GUS showed that BMV-directed GUS expression was inhibited to levels equivalent to those in mab1-1 yeast.

mab1-1 mutation inhibits 1a-induced stabilization of 2a mRNA. In wild-type yeast, co-expression of 1a increases 2a mRNA accumulation approximately 5-fold, with a concomitant increase in 2a protein accumulation (M. Ishikawa, et al., supra, 1997 and FIG. 5). As found for the original mab1-1 strain (M. Ishikawa, et al., supra, 1997), Northern and Western blot analysis showed this 1a-induced increase in 2a mRNA and protein accumulation was inhibited in mab1i yeast (FIG. 4, lower panels).

Figure 4:
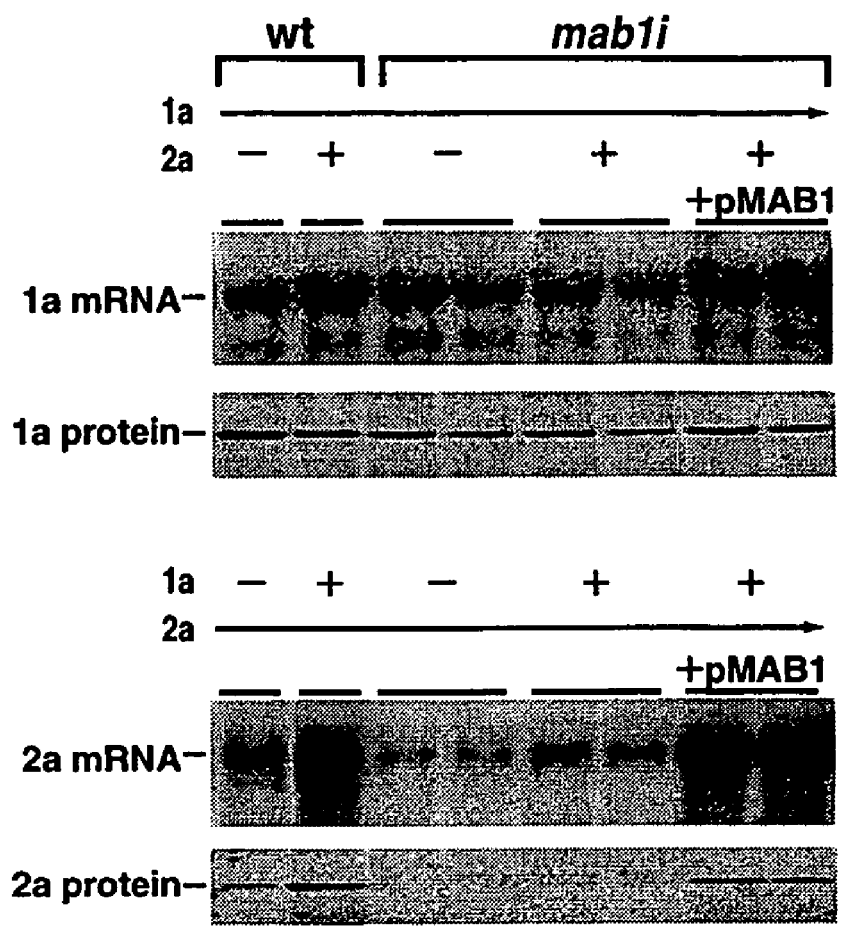

FIG. 4 is a comparison of Northern and Western blots showing accumulation of 1a and 2a mRNA and protein in wild-type YPH500 and mab1i yeast. Total RNA and protein were extracted from yeast expressing 1a and 2a alone or together and analyzed by Northern or Western blots, respectively. Equal amounts of RNA and protein were loaded in each lane. 1a and 2a were expressed from two independent 2μ plasmids with the same ADH1 promotor and termination signals.

Figure 5:
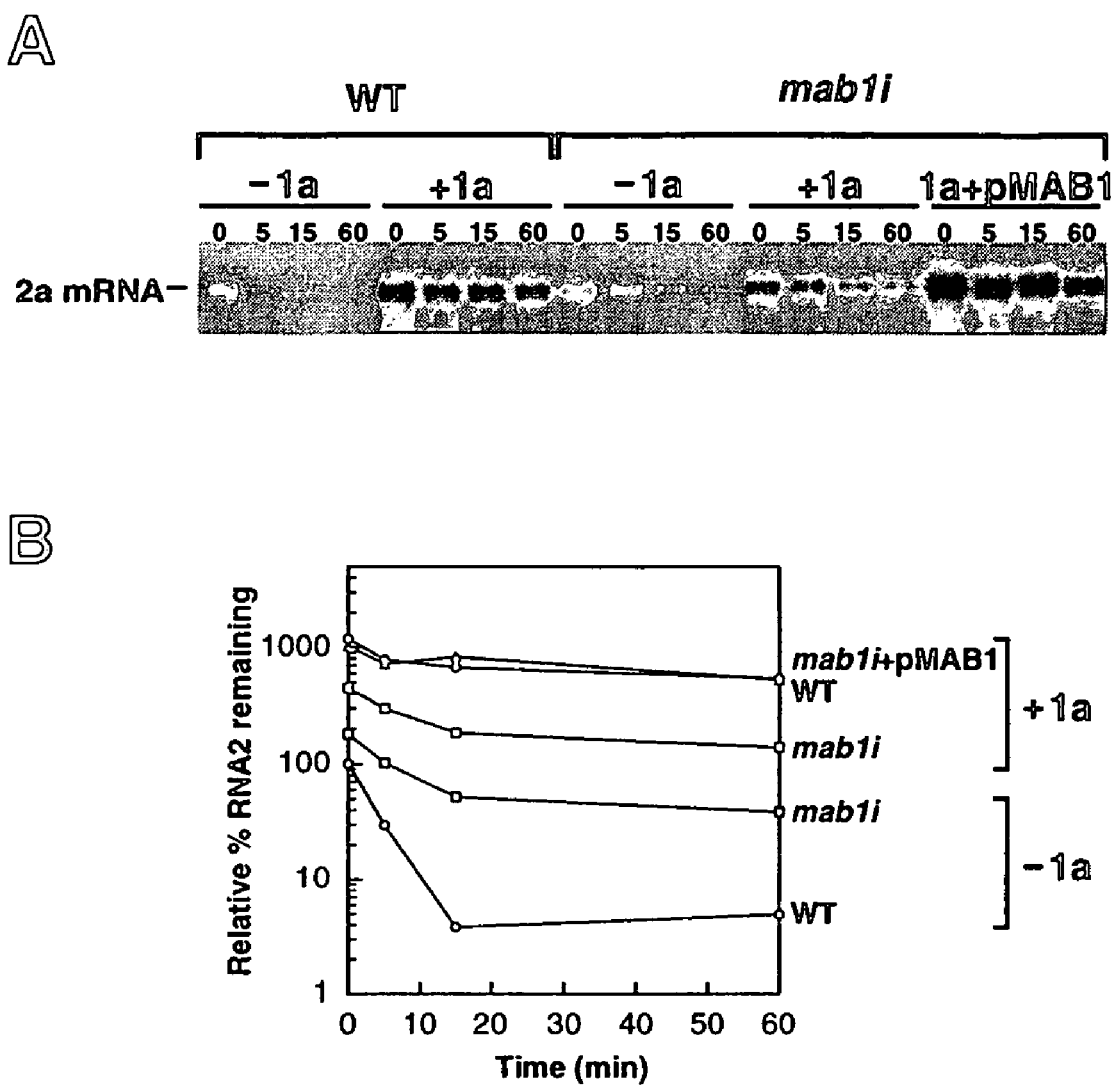

FIG. 5 demonstrates 2a mRNA half-life analysis. FIG. 5A shows wild-type YPH500 and mab1i yeast expressing 2a mRNA alone or in combination with 1a were passaged two times in galactose medium to mid-exponential phase to insure full induction and accumulation of GAL1-promoted 2a mRNA, then transferred to medium containing glucose, which represses transcription from the GALL promotor within a few minutes (Parker, *Meth. Enzym.* 194:415-423, 1991; Johnston, *Microb. Rev.* 51:458-476, 1987). After transfer to glucose medium, yeast were harvested at the indicated times (minutes post transfer to glucose) and total RNA was extracted. 2 μg of each total RNA sample was loaded on a denaturing 1% agarose-formaldehyde gel, transferred to nylon membrane and probed for 2a mRNA. FIG. 5B shows 2a mRNA levels from the experiment in FIG. 5A and similar experiments were measured with a Molecular Dynamics PhosphorImager, expressed as a percentage of the t=0 RNA sample from wild-type YPH500 yeast lacking 1a, and plotted on a semilogarithmic plot vs. time. Averages from three independent experiments are shown. FIG. 5 reveals that, in mab1i yeast, the amount of 2a mRNA recruited by 1a into this highly stable state is reduced by approximately 80%. By contrast, in the absence of 1a, basal 2a mRNA stability and accumulation is increased in mab1i yeast relative to wild-type YPH500 yeast (FIG. 5B). Thus, MAB1 affects the state of at least some RNAs in the absence of the viral 1a protein. A consequent interference in the ability of viral RNAs to interact with 1a and be recruited into the viral RNA replication complex may be an important cause of inhibited BMV RNA replication in mab1i and mab1-1 yeast.

Isolation of the MAB2 gene. Subcloning the implicated yeast genomic DNA region in YCplac22 as discussed above showed that the mab2-1 mutation was complemented by a DNA fragment spanning from coordinates 1114114 to 1119120 in yeast chromosome IV. This fragment contains one complete open reading frame (ORF) larger than 100 codons and the N-terminal portion of a second open reading frame. However, overlapping fragments that contained the second, partial open reading frame but truncated the first open reading failed to complement mab2-1, showing that complementation was due to the first ORF. This ORF extends from coordinates 1114470 to 1116800 and is designated YDR324C in the standard nomenclature for yeast open reading frames, denoting that it is located in the right arm of chromosome IV, relative position 324 from the centromere, and is in the Crick (3' to 5') strand orientation. We propose to name this gene MAB2.

MAB2 is predicted to encode a 776 a protein (MW≈88 kDa) of unknown function. Following the standard yeast ORF nomenclature, this protein is designated YDR324C in the Yeast Protein Database. The MAB2 protein or Mab2p contains amino acid sequence similarities to the WD40 repeat motif, which is found in G-protein β subunits and in proteins involved in RNA processing, membrane vesicle traffic and signal transduction. This WD-40 motif has been suggested to participate in protein-protein interactions (Neer, E. J., et al., *Nature* 371:297-300, 1994).

An engineered mab2 mutant in which most of the MAB2 coding region was replaced with the yeast URA3 gene did not grow at 30° C., showing that MAB2 is an essential gene.

Isolation of MAB3 gene. Subcloning the implicated yeast genomic DNA region in YCplac22 as discussed above showed that the mab3-1 mutation was complemented by a DNA fragment spanning from coordinates 505713 to 507844 in yeast chromosome XIV. This fragment contains only one complete open reading frame (ORF) larger than 100 codons. This ORF extends from coordinates 507095 to 505866 and is designated YNL064C in the standard nomenclature for yeast open reading frames, denoting that it is located in the left arm of chromosome XIV, relative position 64 from the centromere, and is in the Crick (3' to 5') strand orientation. In our proposed nomenclature, this gene would be designated MAB3. This ORF has already been reported to encode a yeast dnaJ homolog, YDJ1/MAS5 (Caplan and Douglas, *J. Cell Biol.* 114:609-621, 1991; Atencio and Yaffe, *Mol. Cell. Biol.* 12:283-291, 1992).

The MAB3/YDJ1/MAS5 locus encodes a 409 aa protein (MW≈44.6 kDa) that can be farnesylated at a site in the C-terminal region (Caplan, et al., *J. Biol. Chem.* 267:1889-18895, 1992). This protein is present in the cytoplasm and on the endoplasmic reticulum and nuclear envelope (Caplan and Douglas, *J. Cell Biol.* 114:609-621, 1991). Yeast with a complete deletion of this gene grow very slowly at 30° C. and do not grow at 37° C. (Atencio and Yaffe, *Mol. Cell. Biol.* 12:283-291, 1992; Caplan and Douglas, *J. Cell Biol.* 114:609-621, 1991). Thus, MAB3/YDJ1/MAS5 is essential for viability at elevated temperatures and important for optimal growth at lower temperatures.

With HSP70 or HSP90, Ydj1p functions as a molecular chaperone, and is involved in various processes such as, e.g., protein import into the endoplasmic reticulum (Caplan, et al., *Cell* 71:1143-1155, 1992) and mitochondria (Atencio and Yaffe, *Mol. Cell. Biol.* 12:283-291, 1992; Caplan, et al., *Cell* 71:1143-1155, 1992), activation of protein kinase p60$^{v-src}$ (Kimura, et al., *Science* 268:1362-1365, 1995; Dey, et al., *Mol. Biol. of the Cell* 7:91-100, 1996) and steroid hormone receptors (Caplan, et al., *J. Biol. Chem.* 270:5251-5257, 1995) and ubiquitin-dependent protein degradation (Lee, et al., *Mol. Cell. Biol.* 16:4773-4781, 1996).

C. Isolation of OLE-1, a yeast mutant strongly inhibiting bmv-directed gene expression.

To isolate mutants with reduced ability to support BMV-directed gene expression, we used yeast strain YM104 (M. Ishikawa, et al., *Proc. Natl. Acad. Sci. USA* 94:19810-13815, 1997a). YM104 contains plasmids expressing BMV 1a and 2a from the constitutive ADH1 promoter and chromosomally-integrated cassettes expressing B3URA3 and B3GUS from the galactose (gal)-inducible GAL1 promoter. B3URA3 and B3GUS are BMV RNA3 derivatives with the coat gene replaced by the URA3 and GUS genes, respectively. URA3 or GUS expression requires both gal to induce B3URA3 and B3GUS transcription, and BMV 1a- and 2a-directed RNA replication and subgenomic mRNA synthesis (FIG. 6A).

FIG. 6A diagrams a pathway for initiating BMV-directed, RNA-dependent RNA replication and subgenomic mRNA synthesis from DNA.

Figure 6:
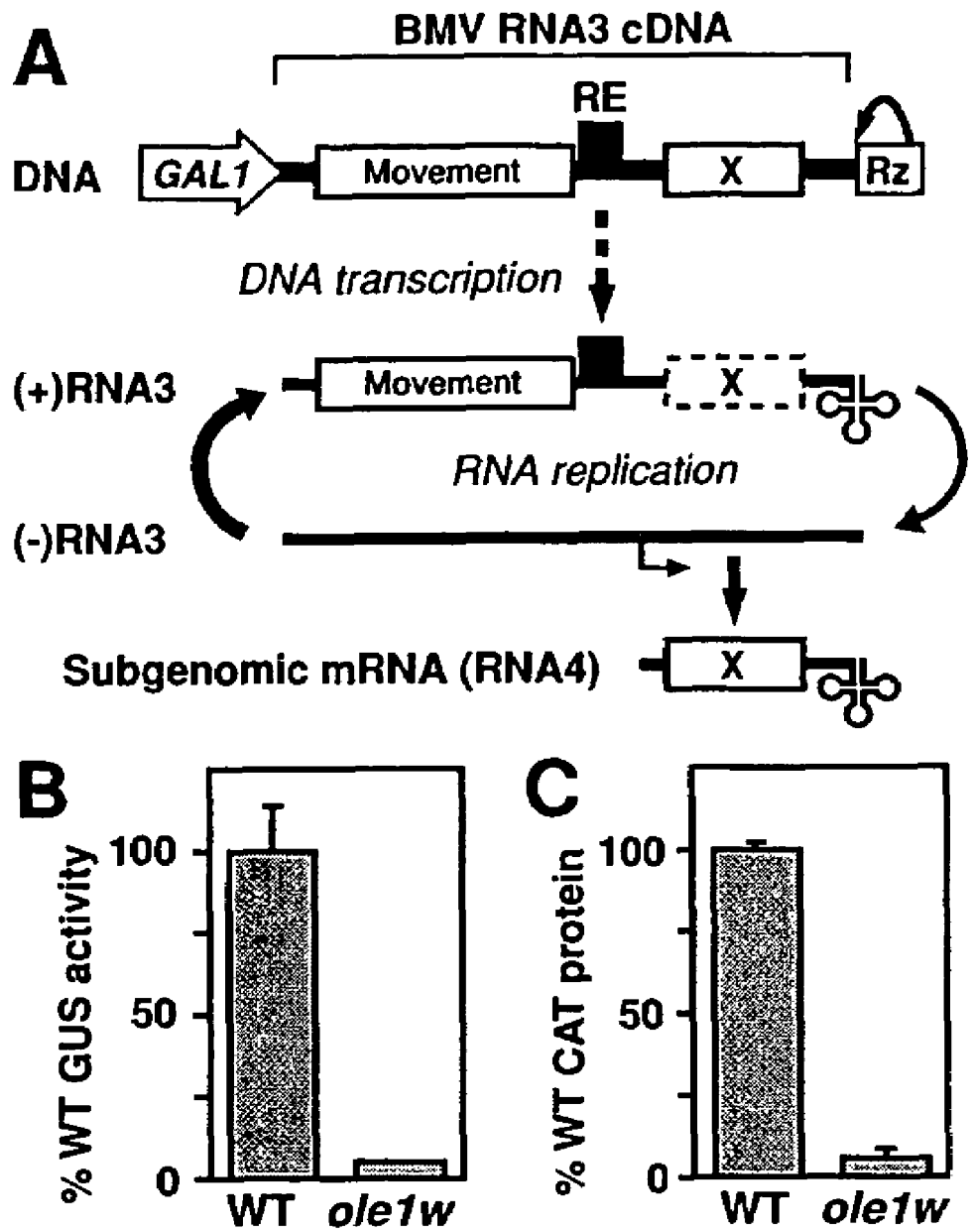

Referring to FIG. 6, top: cDNA-based RNA3 launching cassette including BMV noncoding regions (single lines), movement protein gene, intergenic replication enhancer (RE) 5'-flanking GAL1 promoter and 3'-flanking hepatitis delta virus ribozyme (Rz). ORF X represents the BMV coat gene or its replacements, URA3, GUS or CAT. Upon galactose (gal) induction, cellular RNA pol II synthesizes positive-strand RNA3 transcripts that serve as the templates for 1a- and 2a-directed RNA3 replication and subgenomic mRNA (RNA4) synthesis required to express the coat protein gene or its replacements. The bent arrow below negative-strand RNA3 represents the RNA4 start site. FIG. 6B is a bar graph describing BMV-directed GUS expression in wt YM104 and mutant ole1w yeast. Yeast cells were grown in gal-containing liquid medium for 48 hours and GUS activity per mg total protein was measured. Averages and standard deviations from three independent cultures of each yeast are shown. FIG. 6C is a bar graph describing BMV-directed CAT expression in wt YM104 and mutant ole1w yeast transfected with B3CAT in vitro transcripts. Transfected spheroplasts were incubated 12 hours in gal medium and CAT expression per mg total protein was measured. Data are presented as in panel B.

For mutant isolation, UV-mutagenized YM104 yeast cells were plated on gal medium containing 0.1% 5-fluoroorotic acid to select against cells with BMV-directed URA3 expression. After 5-7 days, about 0.1% of the plated cells developed into colonies. 6,000 such colonies were examined for BMV-expressed GUS activity by filter lift assays. 300 isolates with blue color development lacking or delayed relative to wt YM104 were selected and mated with YM106, which contained no BMV sequences and had the mating type (MATα) opposite to that of YM104 (MATa). Of the resulting 300 diploids, 100 showed restored GUS activity, implying that inhibition of BMV-directed GUS expression in the corresponding YM104-derived parental haploids was due to recessive yeast chromosomal mutations complemented by the YM106 genome. One such GUS-haploid isolate, in which BMV-directed GUS expression was reduced 20-fold, was chosen for further analysis. Complementation studies showed that this mutation was independent of previously described BMV-inhibiting yeast mutations mab1, 2 and 3 (M. Ishikawa, et al., supra, 1997a).

This original mutant strain will be designated ole1w yeast because, as shown below, the causal mutation that inhibits BMV RNA replication maps to the yeast OLE1 gene. w is an allele designation to distinguish this mutation from other ole1 mutations. Ole1w yeast grew normally. Its doubling time in defined gal medium, about 5 hours, paralleled that of wt YM104 yeast. Nevertheless, BMV-directed gene expression was strongly inhibited: GUS activity per mg of total protein in extracts of ole1w yeast averaged 5% of wt YM104 yeast (FIG. 6B). To determine if this inhibition was due to defective DNA-directed transcription or nucleocytoplasmic transport of BE3gus RNA3, these nuclear steps were bypassed by transfecting ole1w yeast with in vitro transcripts of B3CAT, an RNA3 derivative with the coat gene replaced by the CAT gene. Because the ratio of CAT expression in ole1w yeast to wt yeast was equal to that for GUS (FIG. 6B-C), cytoplasmic steps of BMV RNA synthesis must be inhibited in ole1w yeast.

Materials and Methods

Plasmids. pB1CT19 and pB2CT15 (M. Janda and P. G. Ahlquist, supra, 1993) and pB1YT3H and pB2YT5 (J. Chen and P. G. Ahlquist, supra, 2000) were used to express 1a and 2a from the ADH1 and GALL promoters, respectively. pB1YT3H was made by substituting the HIS3 marker gene for the URA3 gene in pB1YT3 (Y. Tomita and M. Ishikawa, unpublished results), a yeast centromeric plasmid with the 1a ORF linked to the GAL1 promoter. All plasmids expressing RNA3 or its derivatives were derived from pB3RQ39 (M. Ishikawa, et al., supra, 1997b) as described. Yeast genomic DNA library ATCC77164 containing yeast strain YPH1 DNA fragments in centromeric vector pRS200 (J. Halbrook and M. F. Hoekstra, supra, 1994) was used to identify the complementing gene.

Yeast strains, cell growth, and transformation. Yeast strain YPH500 and its derivatives (M. Ishikawa, et al., supra, 1997a) were used throughout, except that YMI06 (M. Ishikawa, et al., supra, 1997a) was used for mating. YMI04, the parental strain for mutant isolation, was a YPH500 derivative containing chromosomally integrated B3URA3 and B3GUS expression cassettes and plasmids pB1CT19 and pB2CT15. Ole1Δ::URA3 yeast was constructed by integrative transformation of the YM104 with the NheI-BsrG1 fragment of FIG. 2B with the EcoNI-PacI fragment, containing 90% of the OLE1 ORF, replaced by the transcriptionally active URA3 gene. Isogenic strains ole1w$_i$, and ole1w$_i$' were constructed by integrative transformation of the NheI-BsrG1 fragment (FIG. 7B) containing the mutant ole1w gene into, respectively, ole1Δ::URA3 and an equivalent ole1Δ::URA3 derivative of YPH500. Correct integration was verified by Southern blot analysis.

Yeast cultures were grown and harvested in mid-logarithmic phase (optical density at 600 nm=0.5-0.7) as described (M. Ishikawa, et al., supra, 1997b). Cell pellets were stored at −70° C. for RNA or protein extraction. Tergitol Nonidet P-40 (1%) was added to medium to solubilize unsaturated fatty acids (UFAs) (J. Stukey, et al., supra, 1989). Plasmid transformation was performed with the FROZEN-EZ™ yeast transformation kit (Zymo Research).

RNA Transfection. Capped in vitro RNA transcripts of B3CAT were synthesized from pB3CA101, spheroplasts were prepared from yeast grown 24 hours in gal medium, and RNA transfections were performed as described (M. Janda and P. G. Ahlquist, supra, 1993).

GUS and CAT Assays. GUS filter lifts and quantitative assays were performed as described (M. Ishikawa, et al., supra, 1997b). For CAT assays, yeast lysate was prepared as for quantitative GUS assay but using a different extraction buffer (50 mM Tris, pH 7.5, 5 mM EDTA, 0.1% N-lauroylsarcosine, 0.1% Triton X-100, and 1× protease inhibitors: 0.5 mM phenylmethylsulfonyl fluoride, 2.5 mM benzamidine, 1 μg/ml pepstatin A and 2.5 μg/ml each aprotinin, and leupeptin). CAT protein levels were measured with a CAT ELISA kit (Boehringer Mannheim) and total protein was determined with a Bradford protein assay kit (Bio-Rad).

Western blotting. Protein was prepared as for CAT assays except that the extraction buffer was augmented with 20 mM 2-mercaptoethanol and 2× protease inhibitors and clarified cell lysate was supplemented with 1% SDS and boiled for 5 minutes to inactivate proteases. Total protein was determined with the SDS-tolerant Bio-Rad DC Protein assay (Lowry assay). Cell lysate was electrophoresed and Western blotted as described (M. Restrepo-Hartwig and P. G. Ahlquist, supra, 1996).

Northern blotting. Total yeast RNA isolation, RNA concentration determination by absorbance at 260 nm, agaroseformaldehyde gel electrophoresis and transfer to nylon membrane were performed as described (F. M. Ausubel, et al., supra, 1987; M. Janda and P. G. Ahlquist, supra, 1993). Positive-strand RNA3 and RNA4 were detected with a $^{32}$P-labeled RNA probe complementary to their 3' 200 bases. Negative-strand RNA3 was detected with a $^{32}$P-labeled RNA probe corresponding to the CAT gene (for B3CAT) or coat gene (for B3 and B3CP$^{fs}$) coding sequence (M. Janda and P. G. Ahlquist, supra, 1993). Radioactive signals were measured with a Molecular Dynamics Phosphorimager.

Yeast OLE1 complements mutant defect in BMV-directed gene expression. To identify genes able to complement this recessive defect in supporting BMV-directed gene expression, ole1w yeast cells were transformed with a yeast genomic DNA library carried by shuttle vector pRS200, which bears the yeast TRP1 gene (J. Halbrook and M. F. Hoekstra, *Mol. Cell. Biol.* 14:8037-8050, 1994). Of 20,000 transformants screened by filter lift assays for BMV-directed GUS activity, 5 reproducibly showed a wild-type blue color development. From each of these transformants, a pRS200-based plasmid was isolated by its ability to permit *E. coli* auxotrophic strain KC8 to grow on medium lacking tryptophan (F. M. Ausubel, et al., *Current Protocols in Molecular Biology*, 1987). Each of these plasmids complemented the ole1w mutation when re-transformed into ole1w yeast. Sequencing both ends of the yeast genomic DNA in these plasmids revealed two overlapping fragments of yeast chromosome VII: bases 397187-406757 and bases 398499-407045. The 8.25 kb region common to both fragments contained 5 open reading frames (ORFs) of 100 or more codons and 2 tRNA genes.

Figure 7:
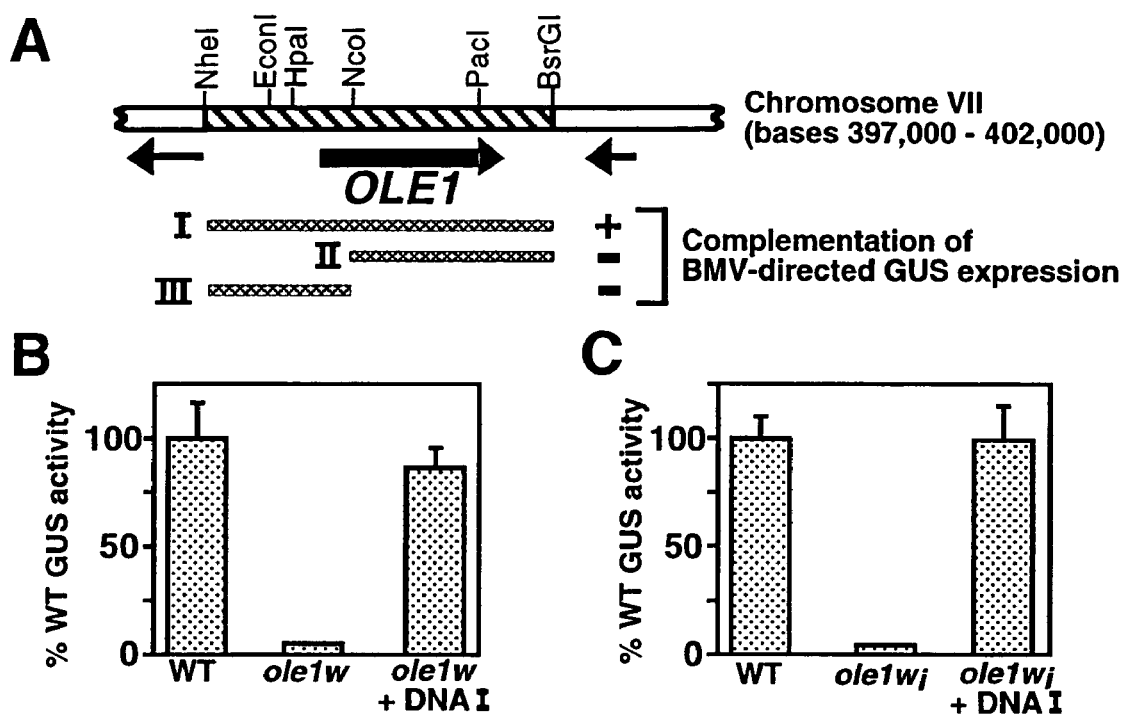

By deletion mapping and filter lift assays for BMV-directed GUS activity, complementing activity was assigned to a 2.9 kb NbeI-BsrG1 fragment containing only the OLE1 ORF (FIG. 7A). When transformed into ole1w yeast, this fragment restored BMV-directed GUS expression to wt levels (FIG. 7B). Moreover, the complete OLE1 gene was required for full complementation (FIG. 7A).

FIG. 7A is a schematic of a 5 kb region of yeast chromosome VII containing the OLE1 ORF (thick arrow), showing 2.9 kb fragment I that complements BMV-directed GUS expression in ole1w yeast and non-complementing fragments II and III. Arrows show flanking ORFs. FIG. 7B is a bar graph demonstrating complementation of BMV-directed GUS expression in ole1w yeast by fragment a of panel A. Wt and ole1w yeast cells were transformed with yeast centromeric plasmid pRS200 carrying fragment a (cDNA) or with the empty plasmid vector. Transformants were grown and GUS activity measured as in FIG. 6B. FIG. 7C is a bar graph demonstrating that isogenic strain, ole1w, constructed by replacing the OLE1 gene in wt YM104 with the ole1w gene from mutant yeast, reproduced the phenotype of the original ole1w mutant.

To determine whether OLE1 was the originally mutated gene or an extragenic suppressor, the ole1w gene was cloned from the mutant yeast by gap repair and used to replace the OLE1 gene in wt YM104 yeast by integrative transformation. The resulting ole1w isogenic strain reproduced the original ole1w mutant phenotype, inhibiting BMV-directed GUS expression to 5% of wt, and this phenotype was suppressed by a plasmid bearing the wt OLE1 gene (FIG. 7C).

To identify the causal mutation in the ole1w allele, restriction fragments were exchanged between the mutant and wt OLE1 genes and the recombinant plasmids were tested for ability to complement ole1w yeast. The mutant phenotype was mapped to a 280 bp DNA fragment encoding $Arg_{167}$-$Leu_{262}$ of the OLE1-encoded protein, Ole1p. DNA sequencing of this region in the wt and mutant genes revealed a single A to G substitution, causing a $Tyr_{262}$ (TAT) to Cys (TGT) substitution in Ole1p.

Figure 8:
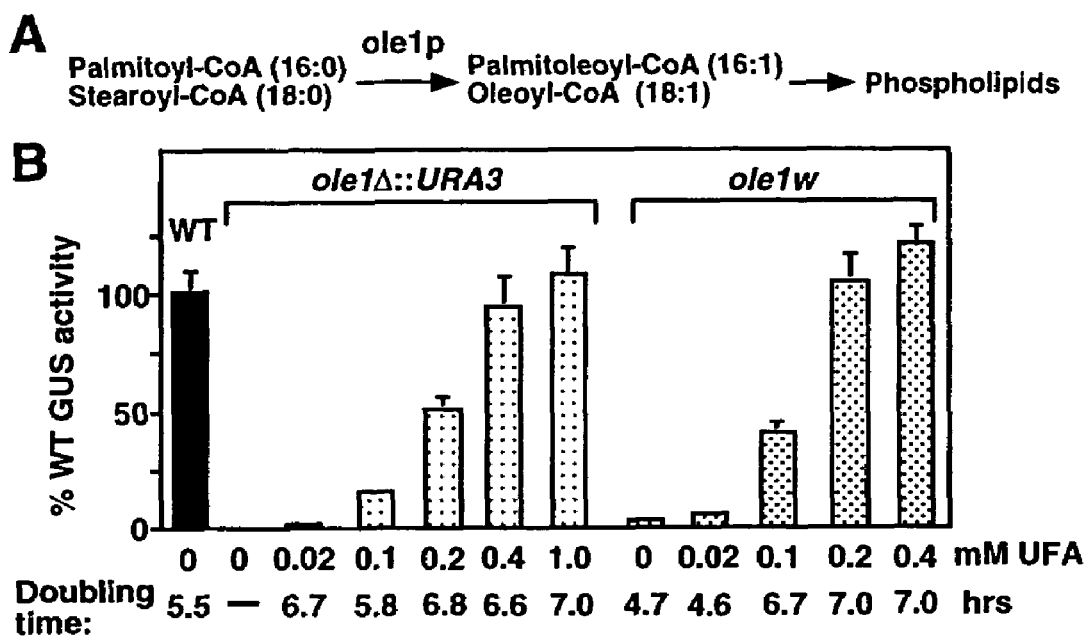

UFAs restore BMV-directed gene expression in ole1w and ole1Δ yeast. Ole1p encodes the Δ9 fatty acid desaturase, an integral ER membrane protein that converts saturated palmitic (16:0) and stearic (18:0) acids into unsaturated palmitoleic (16:1) and oleic (18:1) acids (FIG. 8A). These UFAs exist in yeast cells primarily (>95%) as acyl chains of membrane phospholipids and are important determinants of membrane fluidity and other physical properties. Transcriptional and post-transcriptional regulation of OLE1 by UFAs, SFAs and other conditions are largely responsible for regulating the UFA:SFA ratio and thus membrane fluidity (J. Y. Choi, et al., *J. Biol. Chem.* 271:3581-3589, 1996; Z. Gyorfy, et al., *Biochem. Biophys. Res. Commun.* 237:362-366, 1997). As the only enzyme converting SFAs to UFAs, OLE1 is essential for yeast growth in media lacking UFAs (J. Stukey, et al., *J. Biol. Chem.* 264:16537-16544, 1989). Δ9 fatty acid desaturase is also the rate-limiting, initial enzyme for UFA synthesis in animals (J. M. Ntambi, *J. Lipid Res.* 40:1549-1558, 1999).

Because BMV RNA synthesis is also associated with yeast ER membranes (M. A. Restrepo-Hartwig and P. G. Ahlquist, *J. Virol.* 73:10303-130309, 1999), the function and localization of OLE1 suggested two possible explanations for the inhibition of BMV-directed gene expression in mutant yeast. First, the ole1w mutation might alter the level of UFAs in yeast membranes, which might inhibit BMV RNA replication, subgenomic mRNA synthesis, or both through effects on membrane fluidity or other physical properties. In keeping with this hypothesis, the ole1w mutation ($Tyr_{212}$ to Cys) is located in the predicted catalytic domain of OLE1 (J. Stukey, et al., *J. Biol. Chem.* 265:20144-20149, 1990). Alternatively, Ole1p itself, as an integral membrane protein, could be required as an anchor for the BMV RNA replication complex on the ER.

To determine whether BMV-directed gene expression required Ole1p itself or only URAs, we used integrative transformation to delete the OLE1 ORF of wt YMI04 yeast and replace it with the URA3 gene, creating yeast strain ole1Δ::URA3. As expected, ole1Δ::URA3 yeast was unable to grow in medium lacking UFAs (FIG. 8B). The growth of ole1Δ::URA3 yeast and its ability to support BMV-directed gene expression were then tested in medium supplemented with increasing amounts of UFA. UFA was provided as an equimolar mixture of Ole1p products, palmitoleic and oleic acids, which results in a cellular fatty acid composition similar to that in unsupplemented wt yeast (M. A. Bossie and C. E. Martin, *J. Bacteriol.* 171:6409-6413, 1989). 0.02-0.1 mM UFA was sufficient to restore ole1Δ::URA3 yeast to growth with a wt doubling time, but BMV-directed GUS expression remained inhibited to 5-15% of wt levels (FIG. 8B). Higher UFA levels progressively improved BMV-directed GUS expression, with nearly wt levels restored by 0.4 mM UFA. Thus, UFAs but not Ole1p were important for BMV-directed GUS expression. The ability of ole1 mutant yeast to grow with substantially reduced UFA levels is consistent with the finding that UFA levels in wt yeast membranes are 5- to 9-fold higher than required for growth under optimal conditions (J. Stukey, et al., supra, 1989). The excess UFA is thought to provide extra membrane fluidity required to adapt to environmental changes such as a fall in temperature. Consistent with this, ole1w and ole1w$_i$ yeast lost viability within a few days in storage at 4° C. while wt yeast was stable for several weeks.

Supplementing the original ole1w yeast with UFAs also restored BMV-directed GUS expression (FIG. 8B), implying that the original mutant phenotype was caused by reduced desaturase activity. Ole1w yeast required less UFA supplementation than its ole1Δ::URA3 counterpart to restore a similar level of BMV-directed GUS expression. This is consistent with the fact that ole1w yeast were isolated and grow normally on defined medium lacking UFAs (see above), and so must retain sufficient desaturase activity for cell growth. When either ole1 mutant was grown in high levels of UFA, some increase in doubling time was noted. However, a similar result was seen with wt yeast and mild inhibitory effects of UFAs on yeast growth have been reported previously (S. Zhang, et al., *Genetics* 151:473-483, 1999).

FIG. 8A is a schematic of the pathway of unsaturated fatty acid synthesis and incorporation into membrane phospholipids. Ole1p, Δ9 fatty acid desaturase, synthesizes palmitoleoyl-CoA and oleoyl-CoA by introducing a double bond at $C_9$-$C_{10}$ of palmitoyl-CoA and stearoyl-CoA respectively. FIG. 8B is a bar graph demonstrating that UFAs restore BMV-directed GUS expression in OLE1-deleted yeast (ole1Δ::URA3) and ole1w yeast. Wt YM104, ole1Δ::URA3 and ole1w yeast cells were grown in defined gal medium containing the indicated amount of UFA (an equimolar mixture of palmitoleic and oleic acids; see Results) until mid-log phase. GUS activity was measured as in FIG. 6B. Cell doubling time was calculated from the increase in A600 during log phase growth.

1a and 2a protein accumulation and membrane association in mutant yeast. To facilitate viral RNA accumulation studies below, we made an additional isogenic yeast strain, ole1w$_i$', bearing the ole1w allele but lacking the chromosomally integrated B3URA3 and B3GUS expression cassettes of YMI04 and ole1w$_i$. This ole1w$_i$' strain allowed studying wt RNA3 and RNA3 derivatives introduced on plasmids, while avoiding interference from B3URA3 and B3GUS RNAs in Northern blot analysis of BMV RNA replication products. The initial BMV RNA template used was B3CAT, which combines an easily assayed reporter gene with higher accumulation of BMV RNA replication products than B3GUS.

Figure 9:
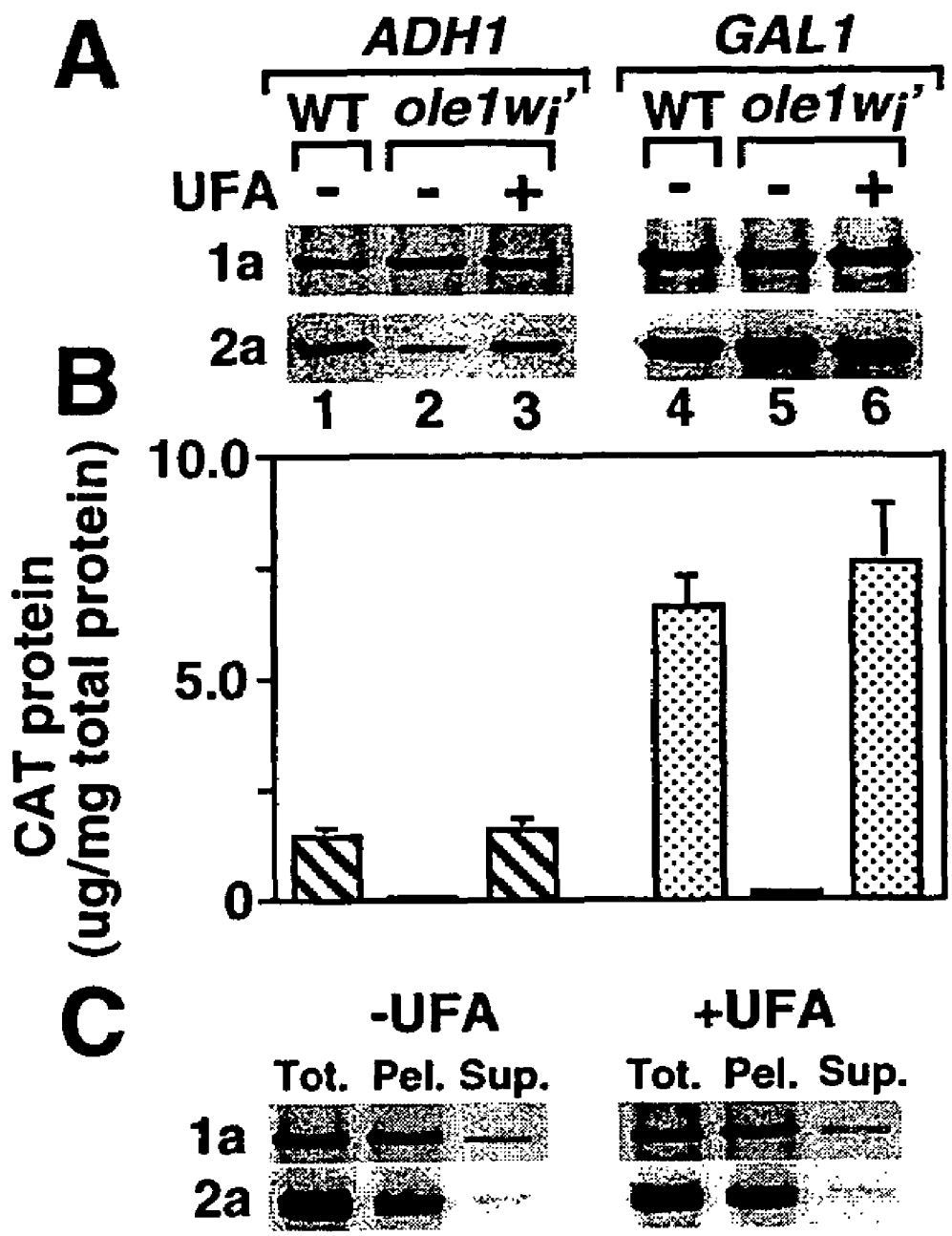

Wt and ole1w$_i$' yeast were transformed with plasmids expressing B3CAT, 1a, and 2a. With ADH1-expressed 1a and 2a, ole1w$_1$' yeast showed wt 1a protein accumulation and slightly reduced 2a protein accumulation (FIG. 9A, lanes 1-3). Because 2a levels can be reduced substantially without inhibiting BMV RNA replication (S. Dinant, et al., *J. Virol.* 67:7181-7189, 1993), it was unclear if this reduction contributed to the ole1w RNA replication phenotype. To resolve this, we tested plasmids expressing 1a and 2a from the GAL1 promoter, which yield higher, more stable 1a and 2a expression in yeast (J. Diez, et al., *Proc. Natl. Acad. Sci. USA* 97:3913-3918, 2000). As intended, GAL1-promoted expression increased 1a and 2a accumulation in wt yeast, and these higher 1a and 2a levels were reproduced in ole1w$_i$' yeast with or without UFA supplementation (FIG. 9A, lanes 4-6).

FIG. 9A is a western blot analysis of 1a and 2a protein accumulation in wt and ole1w yeast containing a plasmid expressing B3CAT and either ADH1-promoted 1a and 2a expression plasmids (lanes 1-3) or GAL1-promoted 1a and 2a expression plasmids (lanes 4-6). Yeast was grown to mid-log phase in gal medium containing no UFA(-) or 0.2 mM UFA (+). Cell lysates were prepared and equal amounts of total protein were electrophoresed and Western blotted as described in Materials and Methods. FIG. 9B is a bar graph demonstrating BMV-directed CAT expression in the yeast cells described in panel A. FIG. 9C demonstrates distribution of 1a and 2a between membrane and soluble cytoplasmic fractions in ole1w yeast with or without the UFA supplementation. Ole1w yeast cells expressing GAL1-promoted 1a, 2a and RNA3 were harvested at mid-log phase and total protein was extracted (Tot.). A portion of the lysate was centrifuged at 10,000×g to yield pellet (Pel.) and supernatant (Sup.) fractions. An equal percentage of each fraction was analyzed by electrophoresis and Western blotting.

BMV-directed CAT expression in ole1w$_i$' yeast with ADH1-expressed 1a and 2a was 5% of wt (FIG. 9B, left side), duplicating the original ole1w phenotype (FIG. 6C). Adding 0.2 mM UFA to the medium restored 2a accumulation and CAT expression to wt levels. The GAL1-promoted increase in 1a and 2a accumulation coincided with a 5-fold increase in BMV-directed CAT expression in wt yeast and UFA-supplemented ole1w$_i$' yeast (FIG. 9B). However, despite wt 1a and 2a levels, CAT expression in unsupplemented ole1w$_i$' yeast with GAL1-promoted 1a and 2a was only 2% of wt (FIG. 9B). Thus, the ole1w mutation inhibited BMV-directed gene expression at one or more steps after 1a and 2a protein production. To provide equal 2a accumulation in wt and ole1 mutant yeast, all subsequent experiments were performed with GAL1-expressed 1a and 2a.

Confocal microscopy and cell fractionation show that 1a and 2a are associated with ER membrane in wt yeast replicating BMV RNA (J. Chen and P. Ahlquist, *J. Virol.* 74:4310-4318, 2000; M. Restrepo-Hartwig and P. G. Ahlquist, supra, 1999). To determine if the ole1w mutation inhibited membrane association of 1a and 2a, ole1w$_i$' yeast with GAL1-expressed 1a, 2a and RNA3 were lysed, membranes were pelleted at 10,000×g, and Western blotting was used to examine the distribution of 1a and 2a between the membrane and soluble cytoplasmic fractions (J. Chen and P. G. Ahlquist, supra, 2000). As shown in FIG. 9C, this distribution was identical in ole1w$_i$' yeast with or without the UFA supplementation, and identical to that in wt yeast (J. Chen and P. G. Ahlquist, supra, 2000). Thus ole1w mutation did not impede membrane association of 1a or its ability to direct 2a to membrane.

Inhibited accumulation of BMV RNA replication products in ole1w$_i$' yeast. To determine whether inhibition of BMV-directed gene expression by ole1w mutation was due to a defect in subgenomic mRNA (RNA4) synthesis or translation, we measured B3CAT RNA4 accumulation in wt and ole1w$_i$' yeast. Positive-strand RNA4 accumulation in ole1w$_i$' yeast was only 2% of wt (FIG. 10, lanes 1-3), fully accounting for the reduction of BMV-directed CAT protein expression (FIG. 9B). Similar inhibition of positive- and negative-strand B3CAT genomic RNA (RNA3) accumulation was seen in ole1w$_i$' yeast (7% and 5% of wt levels). All of these viral RNA accumulation defects were suppressed by medium supplementation with 0.2 mM UFA (FIG. 10, lanes 2-3).

Figure 10:
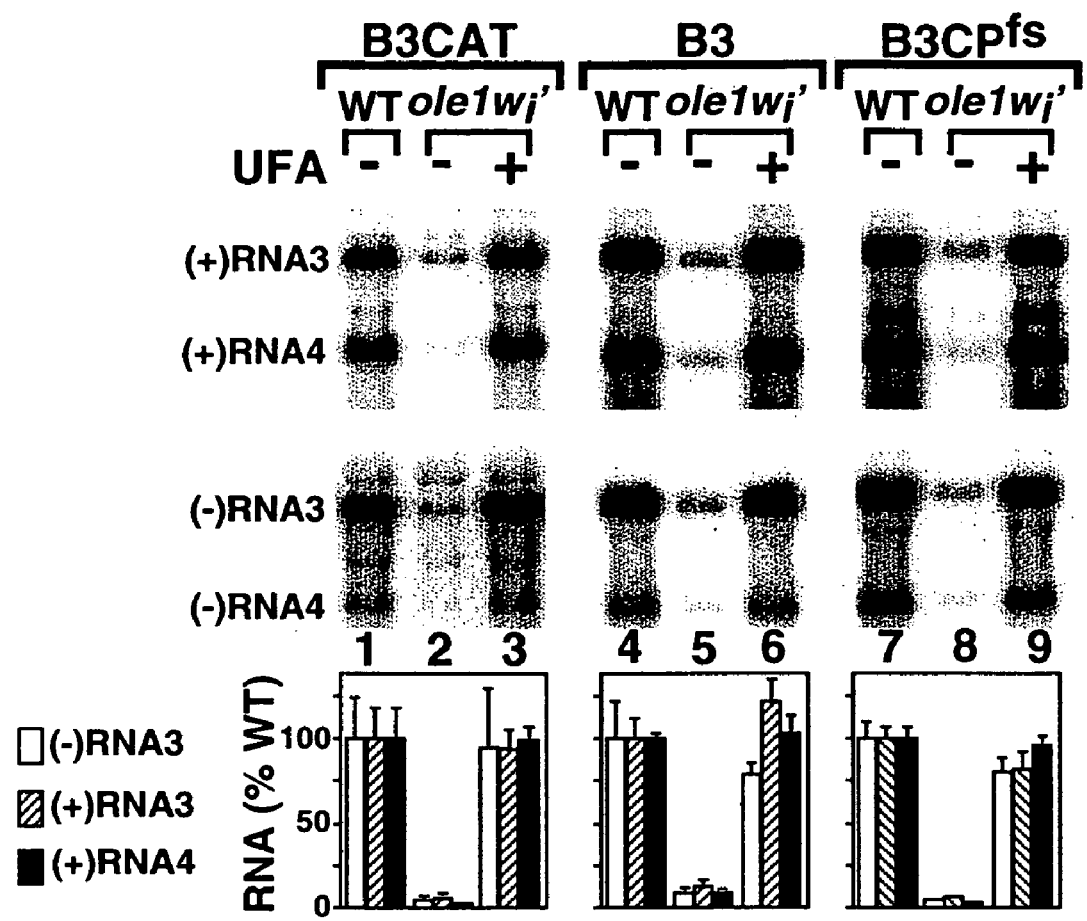

FIG. 10 is a northern blot analysis of RNA3 and RNA4 accumulation in wt and ole1w yeast containing plasmids directing GAL1-promoted expression of 1a, 2a and the indicated RNA3 derivatives. Yeast cells were grown as in FIG. 9. Total RNA was prepared and equal amounts of total RNA were electrophoresed and Northern blotted as described in Materials and Methods. Because negative-strand RNA3 accumulates to 30- to 100-fold lower levels than positive-strand RNA3 in wt yeast, negative-strand blots were printed at higher intensity to facilitate visualization. Negative-strand RNA3 (open bars), positive-strand RNA3 (shaded bars) and positive-strand RNA4 (solid bars) accumulation were measured with a PhosphorImager (Molecular Dynamics) and normalized to that of wt yeast. The histogram shows averages and standard deviations from 3 experiments.

Since B3CAT is not a natural BMV RNA replication template, we also tested wt RNA3 replication in ole1w$_i$' yeast. As shown in FIG. 10, lanes 4-6, negative- and positive-strand RNA3 and positive-strand RNA4 accumulation in unsupplemented ole1w$_i$' yeast were 9%, 13% and 9% of wt. The slightly higher accumulation of wt RNA3 and RNA4 in ole1w$_i$' yeast (13 and 9% of wt levels) relative to B3CAT RNA3 and RNA4 (7 and 2% of wt levels) could be due to expression of small amounts of coat protein, which selectively encapsidate and stabilize BMV RNAs (M. A. Krol, et al., *Proc. Natl. Acad. Sci. USA* 96:13650-13655, 1999). To explore this, we tested B3CP$^{fs}$, in which coat protein expression was eliminated by a four-base frameshifting insertion immediately after the initiating AUG and simultaneous mutation of the second in-frame AUG codon to AUC (M. L. Sullivan and P. G. Ahlquist, J. Virol. 73:2622-2632, 1999). As shown in FIG. 5, lane 7-9, B3CP$^{fs}$ RNA3 and RNA4 accumulated in ole1w$_i$' yeast to 7% and 3% of wt levels, implying that coat protein was largely responsible for increased wt RNA3/4 accumulation relative to B3CAT. To eliminate any effects of coat protein on RNA3 stability and accumulation (see above), B3CP$^{fs}$ was used in all subsequent experiments.

Normal 1a-induced RNA3 stabilization in ole1w$_i$' yeast. In wt yeast lacking 2a, 1a acts through the cis-acting intergenic replication enhancer (RE) of positive-strand RNA3 (FIG. 6A) to dramatically increase stability and accumulation of RNA3 transcripts while inhibiting their translation (M. Janda and P. G. Ahiquist, *Proc. Natl. Acad. Sci. USA* 95:2227-2232, 1998). Multiple results, including parallel inhibitory and stimulatory effects of RE mutations on 1a-induced RNA3 stabilization and RNA3 replication, indicate that these 1a-induced effects reflect the initial recruitment of RNA3 templates from translation to RNA replication (J. Diez, et al., supra, 2000; M. L. Sullivan and P. G. Ahlquist, supra, 1999). To better determine the stage at which RNA3 replication was inhibited in ole1w$_i$' yeast, we tested for 1a-stimulation of RNA3 transcript accumulation in ole1w$_i$' yeast.

Figure 11:
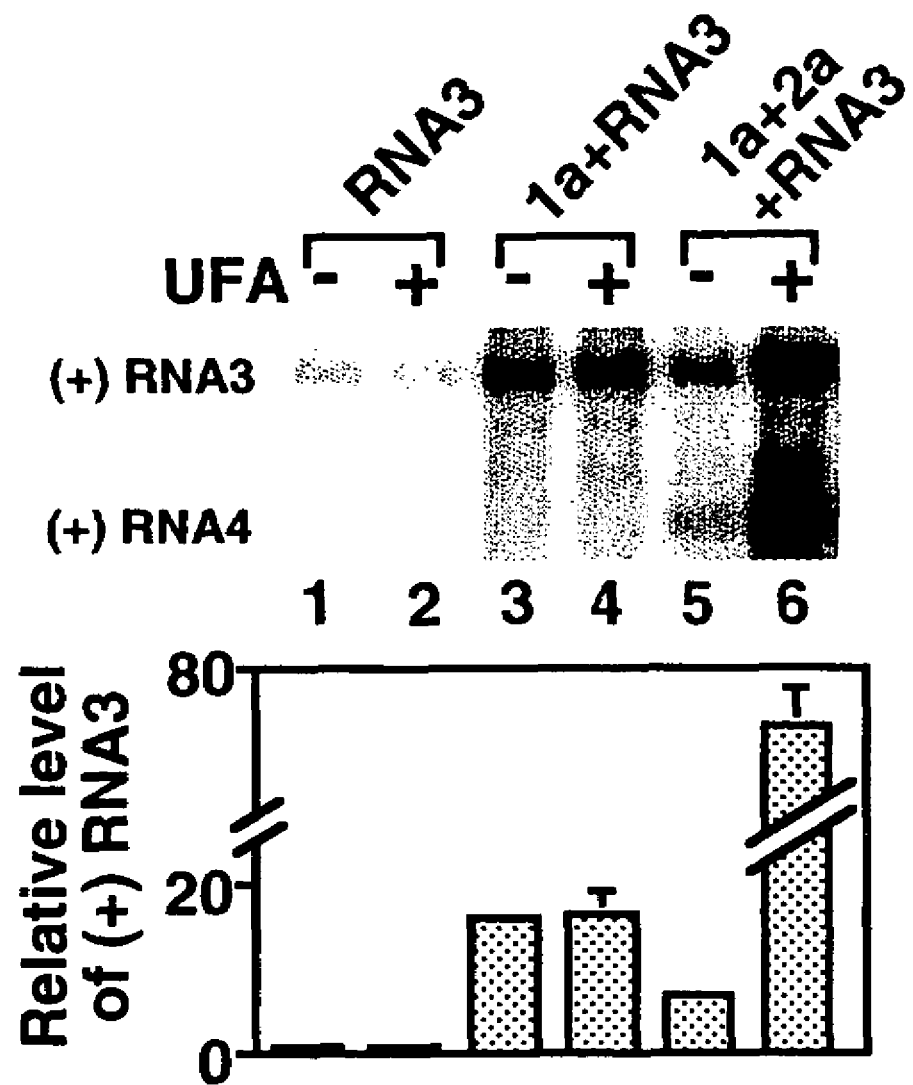

In the absence of 1a and 2a, plasmid-derived, positive-strand RNA3 transcripts accumulated to equal levels in ole1w$_i$' yeast with or without the UFA supplementation that suppresses the ole1w phenotype (FIG. 11, lanes 1-2). Thus, the ole1w mutation did not affect DNA-dependent synthesis or accumulation of RNA3 transcripts. In the presence of 1a, RNA3 accumulation increased 16-fold in ole1w$_i$' yeast, again independent of UFA supplementation (lanes 3-4). Thus, 1a-induced RNA3 accumulation was also not inhibited by the ole1w mutation. Nevertheless, RNA3 replication and subgenomic mRNA synthesis in ole1w$_i$' yeast remained strongly dependent on UFAs (lanes 5-6).

FIG. 11 is a northern blot analysis of BMV-positive-strand RNA3 accumulation in ole1w yeast expressing the indicated BMV components. The B3CP$^{fs}$ derivative of RNA3 was used to avoid effects of coat protein on RNA accumulation (see above). Yeast cells were grown and positive-strand RNA3 accumulation analyzed as in FIG. 10. The histogram shows averages and standard deviations for positive-strand RNA3 accumulation, normalized to that in UFA-supplemented ole1w yeast, from 3 experiments.

Unexpectedly, the ole1w-dependent inhibition of RNA3 replication in lane 5 revealed that less positive-strand RNA3 accumulated in the presence of 1a+2a than with 1a alone (lanes 3-4). Further results below (FIG. 12B, lanes 3-6) show that this 2a effect is independent of UFA supplementation and thus of the ole1w mutant phenotype. Since 2a protein interacts directly with 1a (C. C. Kao and P. G. Ahlquist, supra, 1992) and 2a mRNA is derived from BMV RNA2, another RNA replication template, either 2a or its mRNA might competitively inhibit RNA3 interaction with 1a.

Inhibition of negative-strand RNA3 synthesis in ole1w$_i$' yeast. The negative-strand RNA3 synthesis pathway in yeast is not saturated by DNA-transcribed positive-strand RNA3 templates, so that negative-strand RNA3 accumulation is stimulated by RNA-dependent amplification of positive-strand RNA3 templates (M. Ishikawa, et al., supra, 1997b). Consequently, due to the cyclical nature of wt RNA3 replication (FIG. 6A), the reduced negative-strand accumulation in ole1w$_i$' yeast (FIG. 10) is consistent either with direct inhibition of negative-strand synthesis or with a primary defect in positive-strand synthesis, reducing the templates available for negative-strand synthesis.

To block RNA-dependent positive-strand RNA synthesis and test negative-strand RNA synthesis directly, the wt BMV 5' non-coding region (NCR) of B3CP$^{fs}$ was replaced with the 5' NCR of the yeast GAL1 mRNA in an expression plasmid designated B3(5'GAL,CP$^{fs}$) (FIG. 12A). The resulting B3(5'GAL,CP$^{fs}$) transcript retained the RE region and, like wt RNA3, showed a strong 1a-dependent increase in accumulation (FIG. 12B, lanes 14). Moreover, as expected, B3(5'GAL, CP$^{fs}$) directed UFA-dependent subgenomic mRNA synthesis (FIG. 12B, lane 6). However, even in UFA-supplemented yeast, co-expression of 1a+2a did not produce the dramatic further increase in positive-strand RNA3 accumulation seen for B3CP$^{fs}$ and wt RNA3 (FIG. 12B, lanes 5-6). Rather, with or without UFA supplementation, positive-strand RNA3 accumulation in the presence of 1a+2a was lower than with 1a alone (FIG. 12B, lanes 3-6). Thus, B3(5'GAL,CP$^{fs}$) RNA3 supported little or no BMV-directed positive-strand RNA3 synthesis, confirming prior results that the wt RNA3 5' NCR contains signals required for positive-strand synthesis (M. Ishikawa, et al., supra, 1997b).

Thus, for B3(5'GAL,CP$^{fs}$), the only templates for negative-strand RNA3 synthesis were provided by GAL1-promoted DNA transcription, which was unaffected by the ole1w$_i$' mutation (FIG. 12B, lanes 1-2). Nevertheless, as shown in FIG. 12C, negative-strand RNA accumulation for B3(5'GAL, CP$^{fs}$) in ole1w$_i$' yeast was only 10% of that in wt yeast or ole1w$_i$' yeast supplemented with UFAs (lanes 1-3). Thus, in unsupplemented ole1w$_i$' yeast, BMV RNA replication was inhibited at or before negative-strand RNA3 synthesis.

FIG. 12 demonstrates inhibition of negative-strand RNA3 synthesis in ole1w yeast. FIG. 12A is a schematic of B3(5'GAL, CP$^{fs}$) and its parent B3CP$^{fs}$, indicating cis-acting elements required for template recruitment (RE), negative-strand initiation and positive-strand initiation. B3(5'GAL, CP$^{fs}$) was constructed by replacing the complete viral 5' NCR of B3CP$^{fs}$ with 5'NCR of yeast GAL1 mRNA. FIG. 12B is a northern blot analysis of positive-strand RNA3 accumulation in wt and ole1w yeast expressing the indicated BMV components. Yeast cells were grown and the amount of positive-strand RNA3 in each sample was analyzed as described in FIG. 10. FIG. 12C is a northern blot analysis of negative-strand RNA3 accumulation in wt and ole1w yeast expressing 1a, 2a and B3(5'GAL, CP$^{fs}$). The histogram shows averages and standard deviations fro negative-strand RNA3 accumulation, normalized to that in wt yeast, from 3 experiments.

Discussion

The studies presented here show that BMV RNA replication in yeast is severely inhibited by mutation of OLE1, an essential yeast gene encoding the Δ9 fatty acid desaturase required for UFA synthesis. UFA supplementation of an engineered ole1 deletion strain showed that BMV RNA replication did not require the Ole1 protein but rather required UFA levels well above those required for cell growth. These results demonstrate in vivo the functional importance of lipids for BMV RNA replication and, as discussed below, imply an intimate and potentially dynamic relationship between RNA replication factors and the lipid bilayer.

The RNA replication defect in ole1w mutant yeast was traced to a narrow interval in early replication. In ole1w yeast, RNA replication factor 1a carried out several normal functions. 1a still became membrane associated and directed the membrane association of 2a (FIG. 9C). The 2a-independent ability of 1a to stabilize RNA3 transcripts, a function strongly linked to selection of RNA3 templates for replication (J. Diez, et al., supra, 2000; M. L. Sullivan and P. G. Ahlquist, supra, 1999), was also unimpaired in ole1w$_i$' yeast (FIG. 11). Nevertheless, negative-strand RNA3 synthesis was reduced to 10% or less of wt (FIG. 12C). Thus, BMV RNA synthesis was inhibited after initial recognition of the positive-strand RNA3 template but at or before the first phase of RNA synthesis, negative-strand RNA synthesis. While this defect in negative-strand synthesis is sufficient to explain the overall reduction in BMV RNA replication, the results do not rule out additional defects in later steps of positive-strand RNA3 and subgenomic mRNA synthesis. For flock house virus, e.g., complete in vitro replication of viral RNA and positive-strand synthesis in particular depends on glycerophospholipids (S. X. Wu, et al., supra, 1992). Also, the capping functions of SFV nsP1 are activated by lipids, with a requirement for anionic head groups (T. Ahola, et al., *EMBO J.* 18:3164-3172, 1999). While BMV may be subject to similar influences from polar head groups of membrane lipids, the results presented here show that BMV RNA replication is also highly sensitive to the fatty acid composition of the lipid bilayer.

Recently BMV RNA replication was also found to be inhibited by mutation of yeast gene LSM1 (J. Diez, et al., supra, 2000). LSM1 and OLE1 show many disparate characteristics and appear to be involved in distinct aspects of BMV RNA replication. Unlike OLE1, LSM1 is dispensable for yeast growth in minimal medium at 30° C., though it is required at 37° C. The LSM1-encoded protein, Lsm1p, is not membrane associated, but distributed throughout the cytoplasm. Lsm1p is not a biosynthetic enzyme but rather is related to RNA splicing factors and implicated in the metabolism of viral and cellular mRNAs, including the transition of mRNAs from translation to other fates such as degradation and replication (R. Boeck, et al., *Mol. Cell. Biol.* 18:5062-5072, 1998; J. Diez, et al., supra, 2000). Accordingly, LSM1 mutation inhibits 1a-induced stabilization of RNA3, which is unimpaired in ole1w$_i$' mutants (FIG. 11). These results, isolation of additional BMV-inhibiting yeast mutations and other findings suggest that many if not most steps in viral RNA replication depend on distinct host factors (J. Diez, et al., supra, 2000; M. Ishikawa, et al., supra, 1997a).

UFA dependence of RNA replication. Cerulenin, an inhibitor of lipid synthesis, inhibits RNA replication by poliovirus and the alphavirus SFV (R. Guinea and L. Carrasco, *Virology* 185473476, 1990; L. Perez, et al., *Virology* 183:74-82, 1991). While alternate interpretations cannot be ruled out due to cerulenin's ability to inhibit processes other than lipid synthesis (T. Oda and H. C. Wu, *J. Biol. Chem.* 268:12596-12602, 1993), this suggests a possible requirement for continued lipid and/or membrane synthesis. The inhibition of BMV RNA replication in ole1w yeast, however, is not due to a general block to lipid or membrane synthesis. Ole1p is the desaturase that converts newly synthesized SFAs to UFAs. When UFA levels in yeast are limited by ole1 mutations, membrane synthesis proceeds at normal rates but the UFA:SFA ratio in membrane phospholipids drops (J. Stukey, et al., supra, 1989). Moreover, our studies showed that ole1w yeast cells had normal growth rate and size, and this did not change when the cells expressed 1a+2a+RNA3.

The UFA:SFA ratio affects many membrane-associated functions because of its strong effect on membrane fluidity and other physical properties (P. J. Emmerson, et al., *J. Neurochem.* 73:289-300, 1999; M. Shinitzky, *Physiology of Membrane Fluidity*, 1984). Wt BMV RNA replication required approximately 5 times more UFA supplementation than normal growth of mutant yeast (FIG. 8), suggesting that optimal assembly or function of the RNA replication complex requires a highly fluid membrane. After membrane association, rapid diffusion might be required for 1a, 2a or another replication factor to locate a required interaction partner before being trapped in a competing nonproductive interaction. During replication, rotation or translation of membrane-associated RNA replication factors might be required for RNA unwinding, translocation along RNA templates, or necessary cyclical alterations in protein-protein interactions.

In addition to kinetic effects, reduced UFA levels could also impede BMV RNA synthesis by perturbing the form or stability of replication factor interactions. Under reduced UFA levels, increased lipid packing density and membrane microviscosity tend to displace membrane-associated proteins farther into the aqueous phase, altering their potential for interacting with other factors and the position of such interactions relative to the membrane (R. J. Cherry, et al., *Biochimica et Biophysica Acta* 596:145-151, 1980; M. Shinitzky, supra, 1984). Since introducing a cis double bond shifts lipids from a cylindrical to a more cone-shaped profile, UFAs also influence membrane curvature and flexibility (R. Schneiter and S. D. Kohiwein, *Cell* 88:431-434, 1997). Modulating any of these parameters may impede functional interaction of 1a, 2a, viral RNA or host components with each other. Since ole1w mutation did not inhibit 1a association with membrane or 1a-directed membrane association of 2a (FIG. 9C), the required interaction of the N-terminal of 2a with the 1a helicase-like domain (J. Chen and P. G. Ahlquist, supra, 2000) was not affected in ole1w yeast. However, other 1a-2a interactions required for later RNA replication steps may be perturbed. For example, BMV RNA replication also depends on an independent interaction between 1a and the central 2a polymerase domain (E. Smirnyagina, et al., *J. Virol.* 70:4729-4736, 1996).

While negative-strand RNA synthesis was strongly dependent on UFAs in vivo, a preformed, template-dependent negative-strand RNA synthesis activity can be solubilized from membranes of BMV-infected plant cells or yeast expressing 1a, 2a and RNA3 (R. Quadt, et al., supra, 1995). Thus, the UFA requirement may lie in assembly of a functional RNA synthesis complex. Alternatively, in vivo UFA dependence and membrane association of negative-strand RNA synthesis may relate to functions missing from the solubilized, in vitro negative-strand synthesis activity. Anomalous characteristics of the in vitro system include low efficiency of template usage (<0.1% of added template) and a lack of response to the intercistronic replication enhancer, which in vivo directs 1a-dependent RNA3 stabilization and stimulates negative-strand RNA3 synthesis and RNA3 replication approximately 100-fold (R. Quadt, et al., supra, 1995; M. L. Sullivan and P. G. Ahlquist, supra, 1999).

While oleic and/or palmitoleic UFAs were required for BMV RNA replication, oleic acid disrupts poliovirus RNA replication in HeLa cells (R. Guinea and L. Carrasco, supra, 1991) or HeLa cell extracts (A. Molla, et al., *J. Virol.* 67:5932-5938, 1993). These results may be related to more complex effects of oleic acid on HeLa cells. Supplementing ole1 mutant yeast with oleic acid, palmitoleic acid, or other UFAs yields a direct increase in membrane glycerophospholipids containing these UFAs (J. Stukey, et al., 1989). However, treating of HeLa cells with oleic acid resulted in major changes in the synthesis of many lipids, including dramatic increases in synthesis of cholesterol and other neutral lipids, a reduced phosphatidylserine:phosphatidylcholine ratio, and other changes (R. Guinea and L. Carrasco, supra, 1991). Similarly, in HeLa cell extracts, oleic acid inhibited in vitro translation as well as poliovirus RNA replication (A. Molla, et al., supra, 1993).

In conclusion, we find that BMV RNA replication is strongly dependent on UFA levels in vivo. When UFA was limited, ER-associated RNA replication was blocked after 1a and 2a membrane association and RNA3 template recognition and stabilization, but before negative-strand RNA synthesis. The ability to use ole1w mutation to block RNA replication at this stage should help to elucidate the early events in initiating RNA synthesis. Dependence of BMV RNA replication on UFA levels in particular implies a requirement for host membrane fluidity, suggesting that the membrane is not just a static anchoring site for RNA replication complexes. Accordingly, further study of ole1w yeast should help to illuminate the nature and function of membrane association in positive-strand RNA viruses RNA replication.

Since membrane-associated RNA replication appears to be a universal feature of positive-strand RNA viruses of eukaryotes, the replication of other viruses in this class may also be dependent on the fatty acid composition of membrane lipids. The finding that BMV RNA replication is much more sensitive than normal cell growth to reduced levels of UFAs thus suggests that genetic or pharmacological approaches to modulate the lipid composition of host membranes may provide useful antiviral strategies.

D. Proposed Use of MAB1, MAB2. MAB3 and OLE1 Genes to Develop Antiviral Agents and Vector Systems Increasing evidence shows that virus replication involves a complex interplay between viral and host factors at multiple steps of replication. Before the present invention, most cellular factors on which viral replication depends, or that are able to influence viral replication, remained unknown. Identification of such factors herein enables a number of applications to interfere with, to permit, or to optimize virus replication in various cell types. Illustrative, but not exhaustive, examples of the kinds of applications that we envision are given below. The term "host factor" used herein is exemplified by any of the proteins encoded by MAB1, MAB2, MAB3 and OLE1.

As described above, one may obtain the altered genes of the present invention by various means known to one of skill in the art of microbiology. Most simply, one may obtain the yeast gene by probing a yeast gene library with probes obtained by studying the sequence of the gene. These sequences may be obtained from the yeast protein database at YJL124C for MAB1, YDR324C for MAB2 and YDJ1 for MAB3.

Moreover, conservation of many replication principles, sequences and functions across a wide range of different viruses of humans, animals, plants and microbes and conservation of many structures, sequences and functions across a wide range of human, animal, plant and microbe cells means that host factors and host factor genes identified for one virus and cell type will frequently have important practical implications for similar applications regarding other viruses and cell types. Thus, host factors and host functions identified as influencing BMV RNA replication suggest the involvement of related host factors, assemblies and processes in the replication of other viruses whose replication strategy and/or replication genes are related to those of BMV. Using the sequence and other characteristics of host factors involved in BMV replication, directed searches and tests for related factors involved in the replication of other viruses can be conducted, leading to similar applications.

Host factors involved in virus replication will include factors that interact directly with viral proteins, viral nucleic acids, or both. By virtue of their interaction, such factors offer multiple ways to inhibit virus replication. By point mutation, truncation, or similar approaches, derivatives of such host factors could be created that still bind to their respective viral component but lack other functions necessary to support virus replication. Expression of such derivatives can therefore sequester viral components in a nonproductive complex, interfering with viral replication.

Consistent with the above and with other mechanisms of host factor involvement in virus replication, libraries of mutagenized derivatives of one or more host factors involved in virus replication may be created in expression vectors and screened en masse in cells for antiviral activity. Thus, effective antiviral activity may be derived practically from such a host factor gene by empirical means, without requiring detailed understanding of the normal function of the host factor in virus replication or of the mechanism by which resistance is achieved. Moreover, such empirical mutagenesis and screening approaches can be used to optimize or enhance the virus resistance activity of any existing host factor gene or derivative, and/or to lower its cytotoxicity or other side effects.

Alternatively, understanding of host factor function in infected and/or uninfected cells may exist or can be obtained and used to deliberately devise an engineered resistance strategy. For example, host factors or host factor domains able to bind viral proteins or nucleic acids can be identified and linked to other protein domains able to direct the degradation of proteins or nucleic acids, respectively, thus targeting these viral factors for destruction.

In many cases the proper assembly and function of biological complexes is inhibited by altering the normal balance of expression of the components involved, including the overexpression of one or more components relative to other components. Thus, antiviral effects may be achievable not only by decreasing but also by increasing the expression of host factors involved in viral replication.

Homologs of a host factor from the same or other cells may have natural antiviral activity by virtue of being compatible for normal cellular functions but incompatible for interaction with viral components. Overexpression of such homologs could competitively interfere with virus replication by blocking virus access to necessary cellular assemblies or pathways, or by binding non-productively to viral components as envisioned above for host factor mutants.

In some other cases a virus or viral derivative may be unable to replicate or replicate poorly in a particular cell type due to limiting amounts of a host factor or due to imperfect compatibility between that host factor and a viral component. In such cases, increased expression of the relevant host factor, or expression of a more virus-compatible homolog of the host factor from another cell type, may allow or enhance replication of the virus or its derivatives. Such expression might be engineered into the virus itself, or into the cell independently from the virus, and could be useful for enhanced use of viral gene expression vectors, among other uses.

We claim:

1. A method of evaluating a substance as a positive strand RNA antiviral agent, comprising the steps of
   a) exposing a substance to a yeast or mammalian Δ9 fatty acid desaturase enzyme, and
   b) evaluating the effect of the substance on the stability of the enzyme, wherein decrease in stability indicates that the substance is an antiviral agent against positive strand RNA virus.

2. A method of evaluating a substance as a positive strand RNA antiviral agent, comprising the steps of
   a) exposing a substance to a yeast or mammalian Δ9 fatty acid desaturase enzyme, and
   b) evaluating the effect of the substance on the activity of the enzyme, wherein the inhibition of activity indicates that the substance is an antiviral agent against positive strand RNA virus.

3. A method of evaluating a substance as a positive strand RNA antiviral agent, comprising the steps of
   a) exposing a substance to yeast OLE1 desaturase enzyme, and
   b) evaluating the effect of the substance on the stability of the enzyme, wherein decrease in stability indicates that the substance is an antiviral agent against positive strand RNA virus.

4. A method of evaluating a substance as a positive strand RNA antiviral agent, comprising the steps of
   a) exposing a substance to a yeast OLE1 desaturase enzyme, and
   b) evaluating the effect of the substance on the activity of the enzyme, wherein the inhibition of activity indicates that the substance is an antiviral agent against positive strand RNA virus.

* * * * *

UNITED STATES PATENT AND TRADEMARK OFFICE
CERTIFICATE OF CORRECTION

PATENT NO. : 7,611,833 B2 Page 1 of 1
APPLICATION NO. : 10/618896
DATED : November 3, 2009
INVENTOR(S) : Ahlquist et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1292 days.

Signed and Sealed this

Twelfth Day of October, 2010

David J. Kappos
*Director of the United States Patent and Trademark Office*